US012765789B2

(12) United States Patent
Pfeiffer et al.

(10) Patent No.: US 12,765,789 B2
(45) Date of Patent: Oct. 20, 2026

(54) CONTROL DEVICE FOR CONTROLLING A MEASUREMENT SYSTEM FOR MEASURING BLOOD PRESSURE

(71) Applicant: KONINKLIJKE PHILIPS N.V., Eindhoven (NL)

(72) Inventors: Ulrich Joachim Pfeiffer, Eindhoven (NL); Benjamin Stolze, Oosterhout (NL); Stephan Guido Maria Regh, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 792 days.

(21) Appl. No.: 18/009,754

(22) PCT Filed: Jun. 16, 2021

(86) PCT No.: PCT/EP2021/066178
§ 371 (c)(1),
(2) Date: Dec. 12, 2022

(87) PCT Pub. No.: WO2021/255064
PCT Pub. Date: Dec. 23, 2021

(65) Prior Publication Data

US 2023/0218182 A1 Jul. 13, 2023

(30) Foreign Application Priority Data

Jun. 19, 2020 (EP) .................................... 20181063

(51) Int. Cl.
*A61B 5/0225* (2006.01)
*A61B 5/00* (2006.01)
(Continued)

(52) U.S. Cl.
CPC .......... *A61B 5/0225* (2013.01); *A61B 5/0205* (2013.01); *A61B 5/7225* (2013.01);
(Continued)

(58) Field of Classification Search
CPC ... A61B 5/0225; A61B 5/0205; A61B 5/7225; A61B 5/024; A61B 5/0816;
(Continued)

(56) References Cited

U.S. PATENT DOCUMENTS

| | | | | |
|---|---|---|---|---|
| 2011/0152650 | A1 | 6/2011 | Donehoo | |
| 2017/0245769 | A1 | 8/2017 | Niehaus | |
| 2020/0288984 | A1 * | 9/2020 | Ariyama ............ | A61B 5/02141 |

FOREIGN PATENT DOCUMENTS

| | | | |
|---|---|---|---|
| CN | 101612039 | A | 12/2009 |
| DE | 102017110770 | B2 | 8/2018 |

(Continued)

OTHER PUBLICATIONS

International Search Report Dated Sep. 14, 2021 for International Application No. PCT/EP2021/066178 Dated Jun. 16, 2021.

*Primary Examiner* — Tse W Chen
*Assistant Examiner* — Joseph A Tombers
(74) *Attorney, Agent, or Firm* — Brynne J. Corcoran

(57) ABSTRACT

The invention relates to a control device for controlling a measurement system for measuring blood pressure and optionally hemodynamic parameters of a subject. In a first measurement time period $T_1$, for measured pressure pulses, features are determined, which characterize the respective pressure pulse. Based on the features, start values are determined and, based on the start values, a start curve TPW_F-curve is formed. The measurement system is controlled such that, after the start curve has reached a first maximum, a second measurement time period $T_2$ succeeds, wherein a blood pressure value is determined based on the pressure measured in the second measurement time period. It has been found that by using the maximum in the first measurement time period for defining a start point for the actual blood pressure measurement, a blood pressure value
(Continued)

and optionally also hemodynamic parameters of a subject can be determined very accurately and fast.

14 Claims, 11 Drawing Sheets

(51) Int. Cl.
*A61B 5/0205* (2006.01)
*A61B 5/024* (2006.01)
*A61B 5/08* (2006.01)

(52) U.S. Cl.
CPC ............. *A61B 5/024* (2013.01); *A61B 5/0816* (2013.01); *A61B 2562/0247* (2013.01)

(58) Field of Classification Search
CPC ........ A61B 2562/0247; A61B 5/02028; A61B 5/02108; A61B 5/029; A61B 5/02438; A61B 5/7278; A61B 5/02225
See application file for complete search history.

(56) References Cited

FOREIGN PATENT DOCUMENTS

| | | | | | |
|---|---|---|---|---|---|
| EP | 2759257 | B1 | | 7/2014 | |
| EP | 3430992 | A1 | | 1/2019 | |
| JP | 2002034938 | A | | 2/2002 | |
| JP | 2003339650 | A | | 12/2003 | |
| WO | 2014121945 | A1 | | 8/2014 | |
| WO | WO-2018210931 | A1 | * | 11/2018 | ........... A61B 5/7242 |
| WO | 2019211210 | A1 | | 11/2019 | |
| WO | 2020148137 | A1 | | 7/2020 | |

* cited by examiner

CONTROL DEVICE FOR CONTROLLING A MEASUREMENT SYSTEM FOR MEASURING BLOOD PRESSURE

CROSS-REFERENCE TO PRIOR APPLICATIONS

This application is the U.S. National Phase application under 35 U.S.C. § 371 of International Application No. PCT/EP2021/066178, filed on Jun. 16, 2021, which claims the benefit of European Application No. 20181063.7 filed on Jun. 19, 2020. These applications are hereby incorporated by reference herein.

FIELD OF THE INVENTION

The invention relates to a control device for controlling a measurement system for measuring blood pressure of a subject. The invention relates further to the measurement system for measuring blood pressure of the subject, and a control method and a computer program for controlling the measurement system.

BACKGROUND OF THE INVENTION

DE 10 2017 110 770 B3 discloses a method for non-invasively determining a blood pressure value from a tissue pressure signal by means of a pressure cuff applied to an individual. The tissue pressure signal has a sequence of tissue pressure pulse curves, wherein at least two individual tissue pressure pulse curves are identified in the tissue pressure signal. For each identified tissue pressure pulse curve, an amplitude parameter and an area parameter are determined, wherein the amplitude parameter indicates the amplitude of the respective identified tissue pressure pulse curve and the area parameter indicates at least one partial area enclosed by the respective tissue pressure pulse curve. Moreover, for each identified tissue pressure pulse curve, a pulsation power parameter is determined, which describes the shape of the respective tissue pressure pulse curve, on the basis of the amplitude parameter and the area parameter. A parameter function, which describes a functional relationship between the determined pulsation power parameters of the tissue pressure pulse curves and assigned clamping pressures at the pressure cuff or measurement times, is produced, wherein on the basis of this parameter function the blood pressure value is determined.

US 2011/0152650 A1 discloses a method of operating a non-invasive blood pressure monitor having a blood pressure cuff. During operation of the non-invasive blood pressure monitor, the blood pressure cuff is initially inflated at a rapid inflation rate. Once the blood pressure cuff reaches a first pressure, the inflation rate of the blood pressure cuff is reduced from the rapid inflation rate to a measurement inflation rate. The blood pressure cuff continues to inflate at the measurement inflation rate while the non-invasive blood pressure monitor receives signals from the patient. Based upon the signals received from the patient, the non-invasive blood pressure monitor calculates an "initial inflation pressure", wherein the blood pressure cuff is inflated to the calculated initial inflation pressure and then inflation is terminated. In this manner, signals received from the patient during inflation are used to calculate the initial inflation pressure to reduce the amount of time required to make a blood pressure measurement.

EP 3 430 992 A1 discloses a blood pressure measuring system configured to surround a subject's body part, wherein the blood pressure measuring system comprises pressurization means for applying pressure to the body part and a kinking-proof shell. The kinking-proof shell is arranged to be located between the pressurization means and the body part, when the blood pressure measuring system surrounds the body part. The blood pressure measuring system allows measuring the blood pressure very accurately by continuously raising clamping pressure and stopping the rise above systolic blood pressure, but it is desired to reduce the time needed for carrying out the blood pressure measurement and for optional further measurements like hemodynamic measurements.

SUMMARY OF THE INVENTION

It is an object of the present invention to provide a control device for controlling a measurement system for measuring blood pressure and optionally hemodynamic parameters of a subject, which allows for a reduced measurement time. It is a further object of the present invention to provide a measurement system for measuring blood pressure of a subject comprising the control device, and a control method and a computer program for controlling the measurement system.

In a first aspect of the invention a control device for controlling a measurement system for measuring blood pressure of a subject is presented, wherein the measurement system comprises a) a shell configured to encase a part of the subject, through which blood flows, b) a pressure applicator configured to apply, from outside the shell, pressure to the shell and thereby to the encased part of the subject, and c) a pressure sensor configured to measure the pressure on the skin of the encased part of the subject, wherein the control device is configured to control the measurement system such that the pressure applicator increases the applied pressure over time in a first measurement time period with a first slope and in a second measurement time period with a second slope, wherein the first measurement time period and the second measurement time period are temporally arranged in this sequence, the pressure sensor measures the pressure on the skin during the first and second measurement time periods, wherein the measured pressure comprises a plurality of pressure pulses, wherein the control device is further configured to, in the first measurement time period, determine for each pressure pulse of at least some of the plurality of pressure pulses, at least one feature, which characterizes the respective pressure pulse, determine for a respective pressure pulse a start value, to be used for determining the start of the second measurement time period, based on the least one feature, which has been determined for the respective pressure pulse, such that for several pressure pulses, which are present at different times, several start values are determined, form a start curve, to be used for determining the start of the second measurement time period, based on the several start values, and control, after the start curve has reached a first maximum, the measurement system such that the second measurement time period succeeds, to determine a blood pressure value based on the pressure measured in the second measurement time period.

It has been found that by controlling the measurement system such that, after the start curve has reached a first maximum, the second measurement time period succeeds, the start point of the second measurement time period, in which the blood pressure value is determined, can be defined very accurately such that it is reached relatively fast and the measurement within the second measurement time period allows for a very accurate determination of the blood pressure value. Thus, a blood pressure value and optionally also hemodynamic parameters of a subject can be determined very accurately and fast.

The pressure can be measured directly on the skin of the encased part of the subject or indirectly, wherein in the latter case the skin of the encased part of the subject might be provided with a material like a material of a stocking and the pressure on the skin of the encased part of the subject might be measured through this material. This could also be regarded as a measurement of the pressure on the skin covered with the material which might be a fabric.

The at least one feature can directly characterize the respective pressure pulse or indirectly characterize the respective pressure pulse. In the latter case the respective pressure pulse is processed for determining a feature determination pulse and the at least one feature is determined based on the determined feature determination pulse. This will be explained in more detail further below.

In an embodiment the pressure sensor, which is configured to measure the pressure on the skin of the encased part of the subject, is arranged inside the shell. However, the pressure sensor can also be arranged in another way for measuring the pressure on the skin of the encased part of the subject. For instance, a fluid filled pressure sensor pad can be arranged inside the shell and connected via a fluid path, i.e. via a fluid filled tubing, to a pressure sensor outside of the shell, in order to measure the pressure on the skin of the encased part of the subject.

Preferentially the control device is further configured to control the measurement system such that

- the pressure applicator increases the applied pressure over time also in a zeroth measurement time period with a zeroth slope, wherein the zeroth measurement time period is temporally arranged before the first measurement time period, wherein the first slope is smaller than or equal to the zeroth slope,
- the pressure sensor measures the pressure on the skin also during the zeroth measurement time period, wherein the measured pressure comprises at least one pressure pulse, wherein the control device is further configured

- to determine a heart rate value being indicative of the heart rate of the subject based on the at least one pressure pulse of the pressure measured in the zeroth measurement time period and to, after the determination of the heart rate value, determine the first slope based on the determined heart rate value, and control the measurement system such that the first measurement time period succeeds at least initially with the determined first slope.

In particular, also the second slope is smaller than or equal to the zeroth slope. Preferentially, the zeroth slope is the largest slope among the zeroth, first and second slopes. A relatively large zeroth slope allows to traverse the zeroth measurement time period relatively fast, thereby allowing for a further increased speed of measuring the blood pressure value and optionally also hemodynamic parameters. Moreover, by basing the first slope on the determined heart rate value, the accuracy of determining the start of the second measurement time period, in which the actual blood pressure measurement is carried out, can be even further increased.

The control device can be configured to determine the heart rate value also during the first measurement time period and to modify the first slope based on the heart rate value determined during the first measurement time period. By determining the heart rate value also during the first measurement time period and by modifying the first slope based on the heart rate value determined during the first measurement time period, the accuracy of determining the start of the second measurement time period, in which the actual blood pressure measurement and optionally also the measurement of hemodynamic parameters are carried out, can be further improved.

It is preferred that the control device is configured to control the measurement system such that in the zeroth measurement time period the measured pressure comprises at least two subsequent pressure pulses. In particular, the control device is configured to control the measurement system such that in the zeroth measurement time period the measured pressure comprises exactly two subsequent pressure pulses. Thus, the zeroth measurement time period might be stopped and the first measurement time period might be started, after two subsequent pressure pulses have been measured. Two subsequent pressure pulses is a good compromise between traversing the zeroth measurement time period as fast as possible and having a determination of a heart rate value being accurately enough. For instance, based on each of the two subsequent pressure pulses a respective heart rate value can be determined and these heart rate values can be averaged, in order to determine the heart rate value to be used for determining the first slope. It is also possible, for instance, to determine the heart rate value based on the time needed for measuring the two subsequent pressure pulses. In an embodiment the zeroth slope used in the zeroth measurement time period can be, for instance, 8 mmHg/s. It has been found that this zeroth slope finally leads to a fast and accurate measurement of the blood pressure value and optionally also of hemodynamic parameters.

In an embodiment the first slope is larger than the second slope. The relatively large first slope allows to reach the start of the second measurement time period even faster. Moreover, the determined heart rate value is indicative of a temporal pulse width, i.e. the width of a pressure pulse, wherein preferentially the control device is configured to control the measurement system such that the first slope is equal to or larger than 4 mmHg/PW, wherein PW is the temporal pulse width as indicated by the heart rate value. It has been found that this allows for a further improved determination of the start of the second measurement time period.

The control device is further configured to, in the first measurement time period, determine a first blood pressure value based on the start curve, determine the second slope based on the determined first blood pressure value and control, after the start curve has reached a first maximum, the measurement system such that the second measurement time period succeeds at least initially with the determined second slope. In particular, the control device is configured to determine the systolic arterial blood pressure as the first blood pressure value. The determination of the second slope based on the determined first blood pressure value which preferentially is the systolic arterial blood pressure allows for a further improved measurement in the second measurement time period.

In an embodiment the second slope can be determined by providing a maximum mean pressure value to be reached at the end of the second measurement time period, by providing a length of the second measurement time period and by dividing a) the difference between the provided maximum mean pressure value and the mean pressure value at the end of the first measurement time period by b) the provided length of the second time period. As mentioned above, the determined second slope can be an initial slope only, i.e. the second slope might be modified during the second measurement time period, as it will be explained further below. Similarly, the provided length of the second measurement time period, which is used for determining the second slope, which might only be the initial second slope, can also be the initial length of the second measurement time period only. Thus, the actual length of the second measurement time period can be larger or smaller than the provided length of the second measurement time period, wherein the actual length can depend on measurements carried out during the second measurement time period as also explained below. Also the provided maximum mean pressure value, which is used for determining the second slope which might be an initial second slope, can be an initial maximum mean pressure value, wherein the maximum mean pressure value can be modified based on measurements carried out during the second measurement time period. However, it is also possible that the initially determined second slope is used throughout the second measurement time period and hence not modified. Thus, in an embodiment it is also possible that the determined second slope does not change and is constant during the second measurement time period. In this case, also the provided length of the second measurement time period and the provided maximum mean pressure value can be constant.

For providing the maximum mean pressure value, the control device can comprise assignments between first blood pressure values and maximum mean pressure values, wherein these assignments can be predetermined by calibration. In particular, these assignments can be determined by calibration such that they lead to a very accurate blood pressure measurement with a length of the second measurement time period being relatively small, especially as small as possible. For instance, during a calibration procedure, the assignments can be determined such that a deviation between the determined blood pressure value and a known invasively measured blood pressure value, which is used as gold standard and which has been measured at the same time, is smaller than a predefined deviation threshold and the length of the second measurement time period is as small as possible.

The kind of first blood pressure value and/or the assignments preferentially depend on the type of blood pressure value to be finally determined. Moreover, the assignments can be functional assignments, wherein, during the calibration procedure, parameters of the functional assignments are determined such that the respective blood pressure value is calculated very accurately by using a relatively short second measurement time period. For instance, the respective calibration function can include a linear calibration function having two parameters a and b (e.g. maximum mean pressure value=b+a·first blood pressure value), wherein the parameters a and b can be determined by calibration. In an embodiment, in the second measurement time period, the systolic arterial blood pressure or the mean arterial blood pressure should be determined, wherein in this case the parameter a might be 1 and the parameter b might be, for instance, equal to or smaller than 10 mmHg and preferentially equal to or smaller than 5 mmHg. In this case preferentially the first blood pressure value is also the systolic arterial blood pressure.

In an embodiment the control device can also be configured to determine a hemodynamic monitoring parameter like a pulse pressure variation based on the pressure measured in the second measurement time period, wherein in this case the parameter a might be 1 and the parameter b might be 20 mmHg. Moreover, also in this example the first blood pressure value can be the systolic arterial blood pressure. It is preferred that, if the pulse pressure variation and preferentially also if another hemodynamic monitoring parameter should be determined, a parameter b is used, which is larger than the parameter b that might be used for determining the systolic arterial blood pressure or the mean arterial blood pressure based on the pressure measured in the second measurement time period. The parameter b can also be a percentage of the first blood pressure value.

Thus, in an embodiment the maximum mean pressure value can be defined by the function (1+x)·first blood pressure value, wherein also here preferentially the first blood pressure value is the systolic arterial blood pressure. This function can also be used for determining the maximum mean pressure value, if, for instance, the systolic arterial blood pressure, the mean arterial blood pressure or the pulse pressure variation should be determined based on the pressure measured in the second measurement time period. In correspondence with what has been explained above, if the pulse pressure variation should be determined, the parameter x is preferentially larger than the parameter x which is used for determining the systolic arterial blood pressure or the mean arterial blood pressure based on the pressure measured in the second measurement time period.

The provided length of the second measurement time period, which can be used for determining the second slope, can be a predetermined length, wherein this predetermined length can depend on the type of blood pressure value which should actually be determined based on the pressure to be measured in the second measurement time period, i.e. different predetermined lengths can be provided for different types of blood pressure values to be measured. Also this predefined length of the second measurement time period can be predetermined by calibration such that the desired blood pressure value can be very accurately determined based on the pressure measured in the second measurement time period, wherein the provided length of the second measurement time period is still relatively small. It is also possible that the provided length depends on a heart rate (HR) value and/or a respiration rate (RR) value. The HR value and/or the RR value can be measured during the first measurement time period or it can have been measured before. The length of the second measurement time period can be provided such that it covers a predefined number of pulses as defined by the HR value and/or a predefined number of respiration or ventilation cycles, wherein the ventilation cycles can also be defined by a ventilator machine. For instance, the length of the second measurement time period can be provided such that it covers at least five or six pulses or 3.5 respiration or ventilation cycles. Also this length, i.e. how many pulses and/or respiration or ventilation cycles should be covered, can depend on the desired type of blood pressure value or type of hemodynamic monitoring parameter to be determined based on the pressure measured in the second measurement time period. As explained above, the provided length used for determining the second slope can be an initial length which might be shortened or lengthened during the second measurement time period.

It is also possible that the control device comprises direct assignments between first blood pressure values and second slopes, wherein these direct assignments can also be determined by calibration, particularly by determining parameters of corresponding calibration functions. In an embodiment these calibration functions are combinations of the calibration functions used for determining the maximum mean pressure value and length of the second measurement time period to be used for determining the second slope as described above. Thus, the calibrated function can correspond to a division of a) the difference between a maximum mean pressure value and the mean pressure value at the end of the first measurement time period by b) a length of a second measurement time period, wherein the maximum mean pressure value and the length of the second measurement time period can be determined as described above.

In an embodiment the control device is configured to determine during the first measurement time period for a respective pressure pulse a start value by exponentiating the at least one feature with a predetermined exponent. If several features are used for determining a start value for a respective pressure pulse, these several features are each exponentiated with a respective predetermined exponent and the exponentiated features are combined, particularly multiplied.

It is preferred that the control device is configured such that the forming of the start curve based on the several start values includes a low pass filtering of the several start values. The low pass filtering is preferentially a moving average filtering, wherein the filter window can have a length of, for instance, 4 s. The filter window is preferentially centered at the time for which currently an average value is to be determined.

In an embodiment the control device is configured to, in order to determine for a respective pressure pulse at least one feature, provide a feature determination pulse based on the respective pressure pulse, and determine at least one of the following features:

- the difference between the feature determination pulse's maximum systolic pressure and the feature determination pulse's pressure at the end-diastolic point,
- the duration of the respective feature determination pulse,
- the entire area under the respective feature determination pulse,
- the width at half maximum of the respective feature determination pulse, and
- an upper area under an upper part of the respective feature determination pulse.

The duration of the respective pressure pulse preferentially corresponds to the time difference between an end-diastolic point and the following end-diastolic point for the respective feature determination pulse. Moreover, the entire area is preferentially the entire area under the curve of the respective feature determination pulse from an end diastolic point to the following end diastolic point. The area can be a normalized area. For instance, the area can be normalized by scaling it to the difference between the maximum pressure and the minimum pressure of the respective feature determination pulse. The width at half maximum corresponds to the width at 50 percent of the difference between the maximum pressure and the minimum pressure of the respective feature determination pulse. Thus, it is the width at 50 percent of the difference between the pressure of the feature determination pulse at the maximum systolic point and the pressure of the feature determination pulse at an end diastolic point. The upper area is an upper part of the entire are under the feature determination pulse. The upper area can be a normalized upper area, wherein the upper area under the feature determination pulse can be normalized to the difference between the feature determination pulse's maximum systolic pressure and the feature determination pulse's pressure at an end-diastolic point. This upper area can be more sensitive to waveform changes, i.e. to changes of the feature determination pulse, at an applied pressure close to the systolic arterial blood pressure, which can lead to an increased accuracy of determining the systolic arterial blood pressure.

The feature determination pulse for a respective pressure pulse can be obtained, for instance, by subtracting a mean measured pressure from the respective pressure pulse. However, the feature determination pulse for a respective pressure pulse can also be determined in another way. It can also directly be the respective pressure pulse, i.e. the respective measured pressure pulse.

In an embodiment the control device is configured to determine a start value for a respective pressure pulse based on at least one of the following calculations:

- multiplying a) the determined entire area to the power of a predetermined first exponent with b) the determined difference to the power of a predetermined second exponent,
- dividing a) the determined area to the power of a predetermined third exponent by b) the determined duration to the power of a predetermined fourth exponent and multiplying the resulting quotient with c) the determined difference to the power of a predetermined fifth exponent.

In an embodiment the control device is configured to determine a start value for a respective pressure pulse based on a further multiplication with the width at half maximum to the power of a further predetermined exponent. Thus, in an embodiment the above calculation is extended by a multiplication with the width at half maximum to the power of a further predetermined exponent. These different exponents are preferentially predefined and can be predetermined by calibration measurements, wherein by invasive means reference blood pressure values are determined very accurately and the exponents are determined such that the measurement system controlled by the control device yields the very accurately invasively measured blood pressure values with high statistical precision and accuracy. In particular, for the calibration measurement pairs of simultaneously recorded invasive and noninvasive blood pressure values from an adequate number of individuals in different hemodynamic conditions are used. It should be noted that the calibration is preferentially only carried out in a development phase, i.e. not during an actual blood measurement procedure. The calibration can be carried out separately for different shell sizes, i.e. preferentially for different blood pressure cuff sizes, or for different groups of shell sizes. For instance, for different shell sizes or groups of shell sizes, different sets of exponents can be determined by calibration, i.e. for each shell size or for each group of shell sizes a respective set of exponents can be determined. The calculations for determining the start values could also be used for determining the blood pressure determination values.

In an embodiment the control device is further configured to determine a respiration rate value being indicative of the respiration rate based on the pressure measured in the second measurement time period and/or to receive the respiration rate value from another device. In particular, the control device can be configured to determine the respiration rate value online, i.e. while still measuring the pressure in the second measurement time period. Moreover, the other device could be, for instance, a ventilator machine providing the respiration rate value to the control device, which then might also be regarded as being the ventilation cycle.

In an embodiment the control device is configured to stop the second measurement time period as soon as the respiration rate value indicates that the second measurement time period covers 3.5 respiration or ventilation cycles and/or a predetermined maximum measurement time period has been reached and/or a maximum mean pressure value has been reached. This allows to control the measurement during the second measurement time period such that the overall measurement time is not unnecessarily long, thereby allowing for a further reduction of the overall measurement time. The mean pressure value can be calculated by, for instance, averaging the measured pressure over a predefined moving time interval. It can also be calculated by applying a low pass filter to the measured tissue pressure. The low pass filter is preferentially dimensioned such that the mean pressure comprises frequencies below the lowest expected pulse rate only. Preferred low pass filters will be described further below. The mean pressure value might also be regarded as being a non-oscillating DC component of the measured tissue pressure, which increases with increasing inflation.

The predetermined maximum measurement time period preferentially corresponds to 3.5 times an expected maximum respiration or ventilation cycle duration. This expected maximal respiration or ventilation cycle duration could be, for instance, 7.5 s which corresponds to a respiration rate value of 8 respiration or ventilation cycles per minute. The maximum mean pressure value is preferentially larger than the systolic arterial blood pressure, particularly 20 mmHg larger. The systolic arterial blood pressure is here preferentially the first blood pressure value or a blood pressure value which is determined based on the pulses measured during the second measurement time period, wherein in the latter case the maximum mean pressure value is modified during the second measurement time period. Thus, in an embodiment the control device is configured to modify the second slope depending on the maximum mean pressure value and/or based on the respiration rate value determined during the second measurement time period. If the maximum mean pressure value changes during the second measurement time period, because it is, for instance, the systolic arterial blood pressure plus 20 mmHg and because the systolic arterial blood pressure is measured during the second time period and the measured systolic arterial blood pressure changes, the second slope can change depending on the systolic arterial blood pressure measured during the second measurement time period and optionally on the respiration rate value. This can allow for a further improved measurement of the final blood pressure value and of the optional hemodynamic parameters. Generally, the determination of the respiration or ventilation cycle and/or of the blood pressure while measuring in the second measurement time period allows to accurately and fast determine when the respective one of the stop criteria a) the second measurement time period covers 3.5 respiration or ventilation cycles and/or b) a predetermined maximum measurement time period has been reached and/or c) a maximum mean pressure value has been reached is fulfilled. It can also be used, via modifying the slope accordingly, to steer the pressure application in the second measurement time period such that at least one of the stop criteria is reached accurately and fast. In particular, the second slope can be controlled such that, when the mean pressure has reached a value which is equal to the measured systolic arterial pressure plus a predefined blood pressure value like 20 mmHg, the second measurement time period covers 3.5 respiration or ventilation cycles or corresponds to the predetermined maximum measurement time period.

The control device can be configured to determine:

for a respective pressure pulse measured in the second measurement time period a blood pressure determination value based on at least one of the at least one determined feature such that for several pressure pulses, which are present at different times, several blood pressure determination values are determined, wherein the several blood pressure determination values determined for the several pressure pulses and hence for several times form a blood pressure determination curve, the blood pressure value based on the blood pressure determination curve.

In particular, several features can be determined for a respective pressure pulse measured in the second measurement time period, wherein a blood pressure determination value can be determined by combining at least two of the determined features such that for several pressure pulses, which are present at different times, several blood pressure determination values are determined, wherein the several blood pressure determination values determined for the several pressure pulses and hence for several times form the blood pressure determination curve. By using this blood pressure determination curve for determining the blood pressure, the blood pressure can be determined even more accurately. Preferentially, the control device is configured to determine a maximum of the blood pressure determination curve and to determine the blood pressure based on the determined maximum and the measured pressure.

The control device can be adapted to process the several blood pressure determination values, which are obtained for the several pressure pulses, for obtaining a continuous blood pressure determination curve. For instance, an interpolation can be applied and/or a smoothing. In particular, the control device is configured such that the forming of the blood pressure determination curve based on the several blood pressure determination values includes a low pass filtering of the several blood pressure determination values. Also here the low pass filtering is preferentially a moving average filtering, which is preferentially centered at the time for which currently an average value is to be determined.

It is preferred that the control device is configured such that the low pass filtering of the several start values and the low pass filtering of the several blood pressure determination values both use a filtering window, wherein the filtering window for low pass filtering the several start values has a window length being smaller than a window length of the filtering window for low pass filtering the several blood pressure determination values. For instance, the window length for low pass filtering the several blood pressure determination values could be twice the window length for low pass filtering the several start values. In an embodiment the window length for low pass filtering the several blood pressure determination values is 8 s and the window length for low pass filtering the several start values is 4 s. Moreover, in an embodiment the several blood pressure determination values are low pass filtered several times, preferentially twice, whereas the several start values might be low pass filtered only one time. This leads to a stronger low pass filtering of the measurements obtained in the second measurement time period in comparison to the filtering of the measurements obtained in the first measurement time period, which in turn allows for a more accurate determination of the blood pressure based on the blood pressure determination curve. The low pass filtering is preferentially carried out such that heart lung interactions are eliminated in the blood pressure determination curve, in order to allow for the high quality blood pressure determination. For the start curve the elimination of the heart lung interactions is not necessarily required, because a rough estimation of the blood pressure and the ability to detect a maximum of the start curve are sufficient. In an embodiment heart lung interactions detectable on the start curve are even used in the second measurement time period for determining the respiration rate value.

In an embodiment the control device is configured to determine during the second measurement time period for a respective pressure pulse a blood pressure determination value by exponentiating the at least one feature with a predetermined exponent. If several features are used for determining a blood pressure determination value for a respective pressure pulse, these several features are each exponentiated with a respective predetermined exponent and the exponentiated features are combined, particularly multiplied.

The control device is preferentially configured to further determine a hemodynamic monitoring parameter, i.e. a hemodynamic parameter, based on the pressure measured in the second measurement time period. In particular, the control device is configured to determine as the hemodynamic monitoring parameter at least one of a fluid responsiveness parameter (FRP), a cardiac output (CO), a systemic arterial resistance (SAR) and a cardiac power output (CPO). The control device can also be adapted to determine, as a fluid responsiveness parameter (FRP), for instance, a pulse pressure variation (PPV), a systolic pressure variation (SPV) or a stroke volume variation (SPV) based on the pressure measured in the second measurement time period.

In a further aspect of the present invention a measurement system for measuring blood pressure of a subject is presented, wherein the measurement system comprises:

- a shell configured to encase a part of the subject, through which blood flows,
- a pressure applicator configured to apply, from outside the shell, pressure to the shell and thereby to the encased part of the subject,
- a pressure sensor configured to measure the pressure on the skin of the encased part of the subject, and
- a control device as defined in any of claims 1 to 11.

In another aspect of the presented invention a control method for controlling a measurement system as defined by claim 12 is presented, wherein the control method includes:

- increasing the applied pressure over time in a first measurement time period with a first slope and in a second measurement time period with a second slope by using the pressure applicator, wherein the first measurement time period and the second measurement time period are temporally arranged in this sequence,
- measuring the pressure on the skin during the first and second measurement time periods by using the pressure sensor, wherein the measured pressure comprises a plurality of pressure pulses,
- wherein the method further includes
- determining, in the first measurement time period, for each pressure pulse of at least some of the plurality of pressure pulses, at least one feature, which characterizes the respective pressure pulse, determining for a respective pressure pulse a start value, to be used for determining the start of the second measurement time period, based on the least one feature, which has been determined for the respective pressure pulse, such that for several pressure pulses, which are present at different times, several start values are determined, forming a start curve, to be used for determining the start of the second measurement time period, based on the several start values, and controlling, after the start curve has reached a first maximum, the measurement system such that the second measurement time period succeeds,
- determining a blood pressure value based on the pressure measured in the second measurement time period, wherein the method further includes, in the first measurement time period, determining a first blood pressure value based on the start curve, determining the second slope based on the determined first blood pressure value and controlling, after the start curve has reached a first maximum, the measurement system such that the second measurement time period succeeds with the determined second slope.

In a further aspect of the present invention a computer program for controlling a measurement system as defined by claim 12 is presented, the computer program comprising program code means for causing the measurement system to carry out the steps of claim 13, when the computer program is run on the control device of the measurement system.

The control device, method and computer program are preferentially adapted to continuously control the measurement system for carrying out several subsequent blood pressure measurements whilst attached to the subject.

It shall be understood that the control device of claim 1, the measurement system of claim 12, the control method of claim 13, and the computer program of claim 14, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
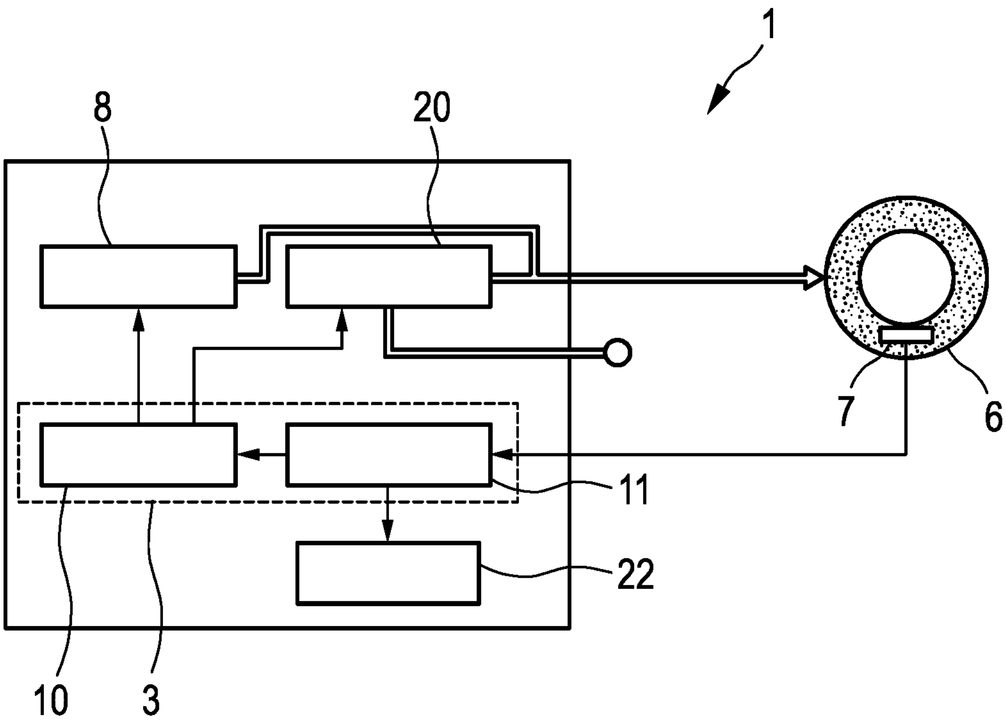
FIG. 1 shows schematically and exemplary an embodiment of a measurement system for measuring blood pressure of a subject in a situation in which a blood pressure cuff of the measurement system is inflated.

FIG. 1 shows schematically and exemplarily a measurement system 1 for measuring blood pressure of a subject.

Figure 2:
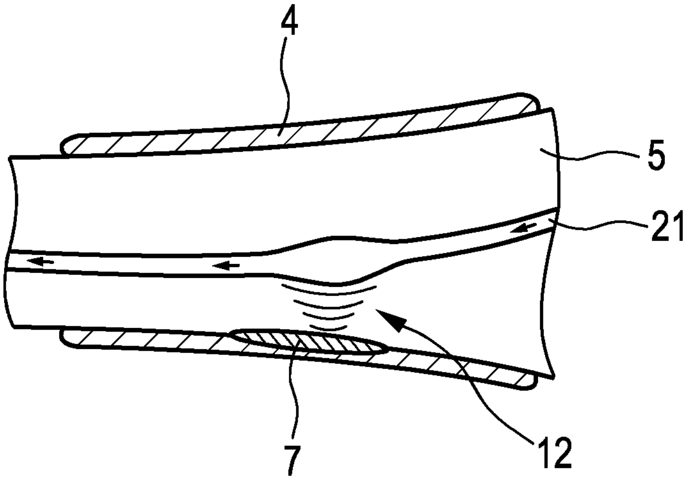
FIG. 2 shows schematically and exemplary a shell of the measurement system encasing an upper arm of the subject.

The measurement system 1 comprises a shell 4 which can be seen in FIG. 2 and which is configured to encase a part 5 of the subject, through which blood flows. In this embodiment the part 5 of the subject is an arm of the subject, wherein in FIG. 2 within the arm 5 a brachial artery 21 is shown and wherein the arrows within the brachial artery 21 indicate the flow direction of the blood away from the heart. The measurement system 1 further comprises a pressure sensor 7 arranged inside the shell 4 and configured to measure the pressure on the outer skin of the encased arm 5 of the subject. The measured pressure can also be regarded as being tissue pressure (TP). As indicated in FIG. 2, a pulse wave within the brachial artery 21 causes a pressure wave 12 which is transmitted to the pressure sensor 7 via the tissue of the arm 5. The shell 4 is not shown in FIG. 1 for clarity reasons.

The measurement system 1 further comprises cuff 6 which encloses the shell 4 and which is inflatable by using a pump 8 for applying, from outside the shell 4, pressure to the shell 4 and thereby to the encased arm 5 of the subject. Since the cuff 6 and pump 8 together enable an application of the pressure to the shell 4 and thereby to the encased arm 5 of the subject, they can be regarded as forming a pressure applicator 6, 8. The shell 4 with the cuff 6 is preferentially a kinking-proof shell cuff as described in WO 2014/121945 A1.

The measurement system 1 further comprises a control device 3 being configured to control the measurement system 1 such that the pressure applicator 6, 8 increases the applied pressure in a pressure increase time period and decreases the applied pressure in a following pressure decrease time period and that the pressure sensor 7 measures the pressure on the skin, i.e. the tissue pressure TP, at least during the pressure increase time period. The control of the measurement system 1 such that the cuff 6 is inflated and hence the applied pressure is increased is illustrated in FIG. 1, i.e. the bold arrow indicates the inflation situation.

Figure 3:
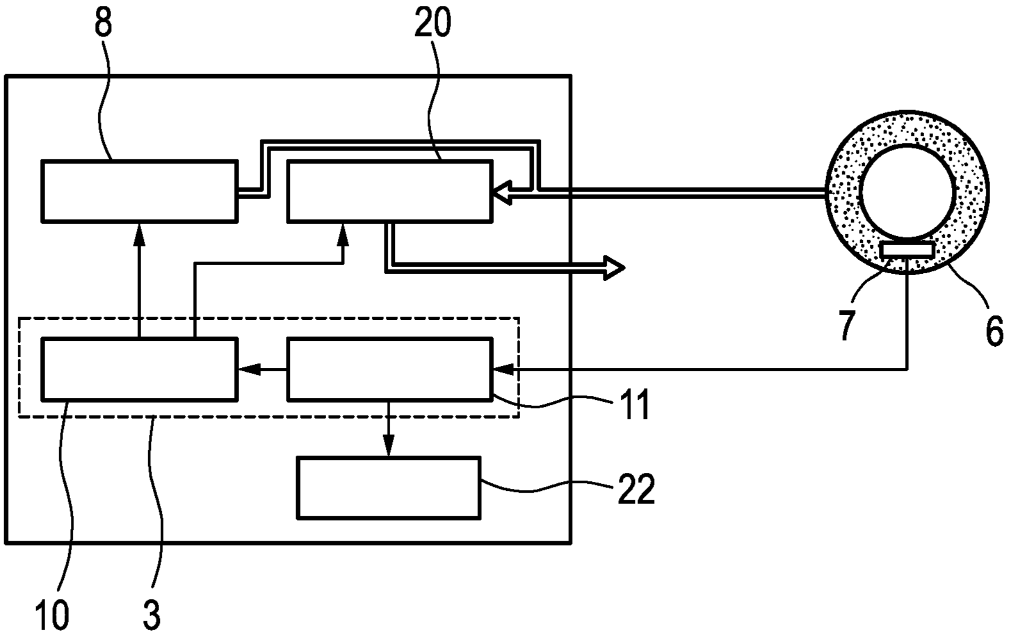
FIG. 3 shows schematically and exemplary the measurement system in a situation in which the blood pressure cuff is deflated.

The measurement system 1 comprises a valve 20 which, when the valve 20 is opened, allows the compressed air within the system to leave the system into the surrounding atmosphere for deflating the cuff In FIG. 3 this deflation situation, in which the pump 8 is switched off, is indicated by the bold arrows.

The control device 3 can be regarded as comprising an actual controller 10 for controlling the pump 8 and the valve 20 and a processor 11, which especially is configured to carry out some calculations that will be explained further below. The measurement system 1 can also comprise a display 22 for displaying, for instance, a measured blood pressure value.

The measured pressure TP has pressure pulses 9 as it will be explained in the following with respect to FIG. 4. It should be noted that FIG. 4 is just used for illustrating aspects of the invention like the pressure pulses 9, but it does not show an embodiment of the invention, which would require that in a first measurement time period a start determination curve is determined, wherein its maximum is used for determining a start of a second measurement time period as it will be explained further below, particularly with reference to FIG. 5.

Figure 4:
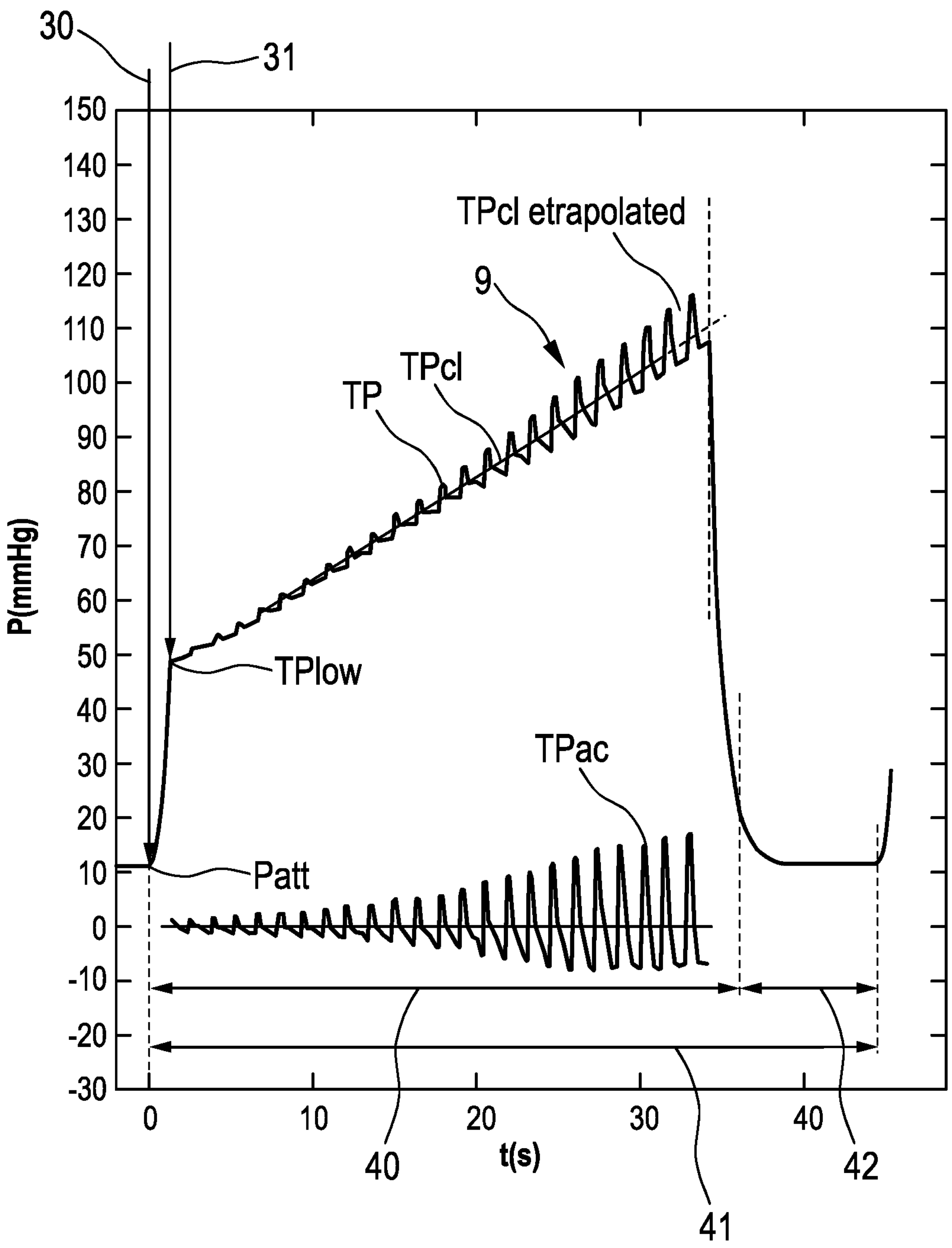
FIG. 4 shows schematically and exemplary a measured tissue pressure and further values derived from the tissue pressure measurement.

As can be seen in FIG. 4, the measured pressure TP versus time t has, as mentioned above, pressure pulses 9. In FIG. 4, a zeroth inflation starts with a tissue pressure TP being an attachment pressure Patt that is the measured tissue pressure in the uninflated cuff 6. This attachment pressure Patt can range, for instance, from 0 to 15 mmHg. An attachment pressure Patt up to 15 mmHg has turned out to not result in venous congestion for more than 12 hours, thereby making the assembly of the shell 4 with the cuff 6 optimally suitable for long term monitoring. For this reason, it is preferred that the attachment pressure Patt is not larger than 15 mmHg. In FIG. 4 the arrow 30 indicates the start of the zeroth inflation. During this zeroth inflation the part of the overall tissue pressure range, which has no or substantially no information for the determination of the blood pressure, shall be passed as fast as possible. Therefore, the inflation rate is preferentially as large as possible during this zeroth inflation. For instance, the inflation rate with respect to the tissue pressure TP can be equal to or larger than 8 mmHg/s. This zeroth inflation period with the fast inflation rate ends at a tissue pressure value which is indicated in FIG. 4 by "TPlow". The tissue pressure value TPlow also indicates the start of the first inflation time period with the slower first inflation rate. In FIG. 4 this start of the first inflation time period, which can also be regarded as being a slow inflation period, is indicated by the arrow 31.

In FIG. 4 the time interval 40 indicates an inflation-deflation time period from the start 30 of fast inflation until the tissue pressure TP has dropped below 20 mmHg during the fast deflation, in order to allow venous return. The time period 41 indicates a cycle time being the time between a start of a measurement and a start of a following measurement and the time period 42 indicates a break period being the difference between the inflation-deflation time period 40 and the cycle time 41.

As mentioned above, FIG. 4 is just used for illustrating aspects of the invention, without showing an embodiment of the invention, which requires that in a first measurement time period a start determination curve is determined, wherein its maximum is used for determining a start of a second measurement time period. An embodiment of the invention is illustrated in FIG. 5.

Figure 5:
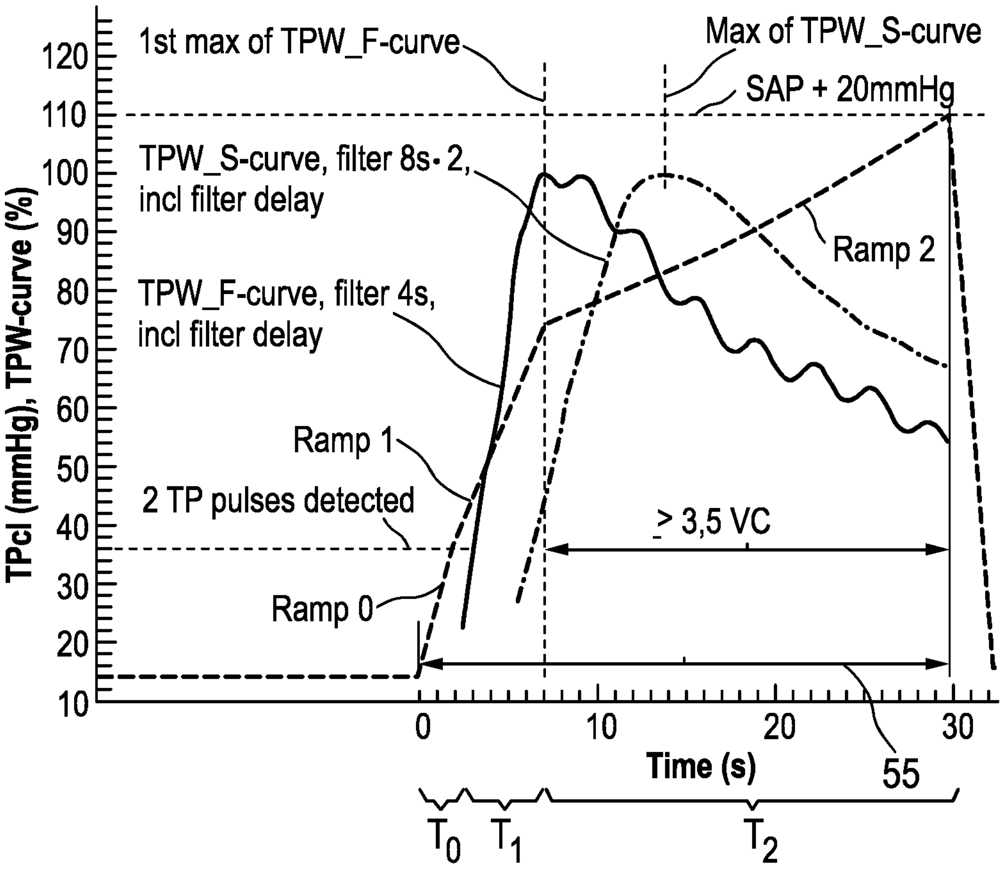
FIG. 5 shows schematically and exemplary a measured tissue pressure and further values derived from the tissue pressure measurement in accordance with an embodiment of the invention.

As can be seen in FIG. 5, the control device 3 is preferentially configured to control the measurement system 1 such that the pressure applicator 6, 8 increases the applied pressure over time in a zeroth measurement time period To with a zeroth slope, in a first measurement time period $T_1$ with a first slope and in a second measurement time period $T_2$ with a second slope, wherein the zeroth measurement time period To, the first measurement time period $T_1$ and the second measurement time period $T_2$ are temporally arranged in this sequence. The multiple pressure increases in the different measurement time periods can be regarded as different ramps which are denoted in FIG. 5 with Ramp0, Ramp1 and Ramp2. The pressure sensor 7 measures the pressure TP on the skin during the zeroth, first and second measurement time periods, wherein the measured pressure TP comprises a plurality of pressure pulses. The corresponding inflation phase is indicated in FIG. 5 with the reference sign 55.

In the zeroth measurement time period To, which could also be regarded as being a fast inflation period, the control device 3 controls the measurement system 1 such that the valve 20 is closed and the pump 8 inflates the cuff 6 with the zeroth rate, i.e. with the zeroth slope. In the subsequent first measurement time period $T_1$ the control device 3 also controls the measurement system 1 such that the valve 20 is closed, but the pump 8 is controlled such that the inflation of the cuff 6 is continued with the first rate, i.e. the first slope which is smaller than the zeroth slope. In the then following second measurement time period $T_2$ the control device 3 controls the measurement system 1 still such that the valve 20 is closed, but the pump 8 is controlled such that the inflation of the cuff 6 is continued with the second rate, i.e.

the second slope which is also smaller than the zeroth slope. Preferentially, the first slope is larger than the second slope.

The control device 3 is further configured to control the measurement system 1 such that the measured pressure TP comprises at least one pressure pulse in the zeroth measurement time period $T_0$ and to determine a heart rate value HR being indicative of the heart rate of the subject based on the at least one pressure pulse of the pressure TP measured in the zeroth measurement time period To and to, after the determination of the heart rate value HR, determine the first slope based on the determined heart rate value HR, and control the measurement system 1 such that the first measurement time period $T_1$ succeeds with the determined first slope. The control device 3 can be configured to determine the heart rate value HR also during the first measurement time period $T_1$ and to modify the first slope based on the heart rate value HR determined during the first measurement time period.

The pressure pulses are caused by the pulsating heart, wherein the heart rate value can be determined, for instance, based on the width of the respective pressure pulse or based on the number of pressure pulses in a period of time. The determined heart rate value is preferentially indicative of a temporal pulse width, i.e. the width of a pressure pulse, wherein the control device 3 can be configured to control the measurement system 1 such that the first slope is equal to or larger than 4 mmHg/PW, wherein PW is the temporal pulse width as indicated by the heart rate value.

In this embodiment the control device 3 is configured to control the measurement system 1 such that in the zeroth measurement time period To the measured pressure TP comprises at least two subsequent pressure pulses, preferentially exactly two subsequent pressure pulses. Thus, the control device 3 is preferentially configured to determine the heart rate value based on the pressure pulses of the pressure TP measured in the zeroth measurement time period as soon as two subsequent pressure pulses have been measured. In particular, the heart rate value is determined based on the first two measured subsequent pressure pulses, whereafter the measurement proceeds with the first measurement time period.

Also the zeroth measurement time period, like the zeroth inflation time period described above with reference to FIG. 4, can start with an attachment pressure Patt which can range, for instance, from 0 to 15 mmHg, i.e. it is preferred that the attachment pressure Patt is not larger than 15 mmHg. During the zeroth measurement time period the part of the overall tissue pressure range, which has no or substantially no information for the determination of the blood pressure, shall be passed as fast as possible, wherein still enough information should be gathered for measuring the heart rate value HR. Therefore, the zeroth inflation rate is preferentially as large as possible during this zeroth measurement time period To, wherein it is still possible to determine the heart rate accurately enough. For instance, the zeroth slope with respect to the tissue pressure TP can be equal to or larger than 8 mmHg/s, but it can also have another value.

The control device 3 is further configured to, in the first measurement time period $T_1$, determine for each pressure pulse of at least some of the plurality of pressure pulses, at least one feature, which characterizes the respective pressure pulse. Preferentially, for each pressure pulse several features are determined. This will be explained in the following.

FIG. 4 also illustrates a mean pressure TPcl that can be regarded as being a tissue clamping pressure affecting the tissue when the cuff 6 is attached to the arm 5, for instance, to the upper arm, of the subject. The mean pressure TPcl can be calculated by applying a low pass filter to the tissue pressure TP, wherein the low pass filter might be located within the control device 3, particularly in the processor 11 of the control device 3. The low pass filter is preferentially dimensioned such that the mean pressure TPcl comprises frequencies below the lowest expected pulse rate (PRni) only. Preferred low pass filters will be described further below. The control device 3 is preferentially configured to determine an alternating component TPac of the tissue pressure by subtracting the mean pressure TPcl from the measured tissue pressure TP, i.e. TPac=TP−TPcl. In FIG. 4 the TPac curve is shown enlarged by a factor of 2, in order to improve visibility of this curve.

During the zeroth, first and second measurement time periods TP pulse curves and/or TPac pulse curves are recorded, which may be analyzed and parameters are calculated simultaneously, i.e. online, wherein the TP pulse curves and/or the TPac pulse curves have tissue pressure waveforms (TPW) comprising information which allows for an accurate determination of the blood pressure. Since the blood pressure is noninvasively measured (although it nevertheless has an accuracy which is comparable to the accuracy of invasively measured blood pressure), it can be abbreviated with niBP meaning "noninvasive blood pressure". A TPac pulse curve is schematically and exemplarily shown in FIGS. 6 to 9.

In the following the TPac pulse curves are used for determining features for the pressure pulses. The TPac pulse curves can therefore be regarded as being feature determination pulse curves or feature determination pulses. FIGS. 6 to 9 hence show feature determination pulse curves or feature determination pulses 29 being TPac pulses. In another embodiment the feature determination pulses can also directly be the TP pulse curves, i.e. the pressure pulses can be directly used for determining the features.

It has been observed that, when increasing the clamping pressure, i.e. when increasing the pressure applied to the arm 5 via the cuff 6, the diastolic tissue pressure pulse form changes from a rather pointed shape to a flattened diastolic shape when crossing the mean arterial pressure (MAP) as can be seen in FIG. 7A, 7B, 7C of WO 2018/210931 A1. This behavior can be modelled by the changes of several TPW_parameters. TPW_parameters can be extracted from the TP pulse curves as described in the document WO 2018/210931 A1.

In an embodiment, the control device 3 is configured to determine a TPP difference between a maximum measured pressure and a minimum measured pressure of the respective feature determination pulse 29 as a feature, i.e. as a TPW_ parameter, for the respective pressure pulse. This feature, i.e. this TPW_parameter, will be described with reference to FIG. 6 in the following.

Figure 6:
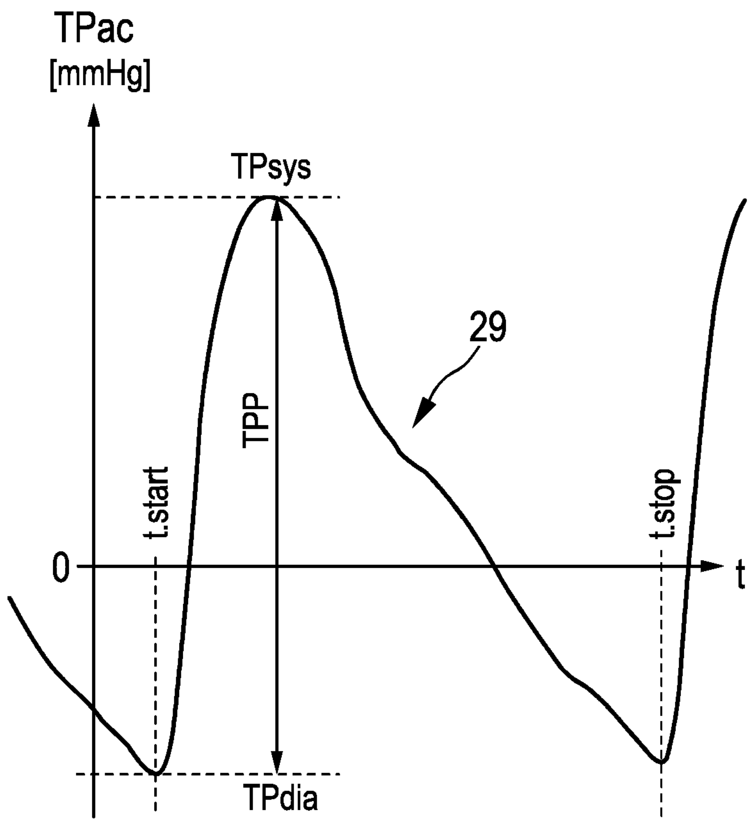
FIGS. 6 to 9 illustrate a calculation of several features for a pressure pulse of the measured tissue pressure.

The difference TPP is a difference of a feature determination pulse's maximum systolic pressure TPsys and the feature determination pulse's pressure at an end-diastolic point (TPdia), which is preferably the minimum pressure of the respective feature determination pulse. In FIG. 6 and also in FIGS. 7 and 8 the terms "t.start" and "t.stop" indicate the start and the end, respectively, of the respective pulse 29.

Figure 7:
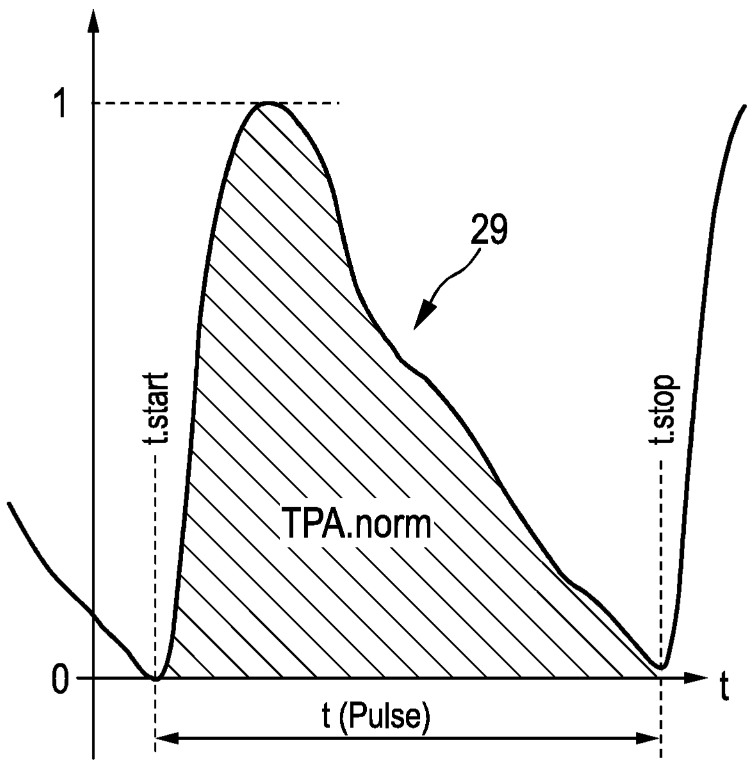

The control device 3 can also be configured to determine the pulse duration (t(Pulse)) being the time difference between an end-diastolic point and a following end-diastolic point of the feature determination pulse 29. This feature can also be defined as being the temporal difference between the start of the respective pulse (t.start) and the end of the respective pulse (t.stop). This feature is indicated in FIG. 7.

Figure 8:
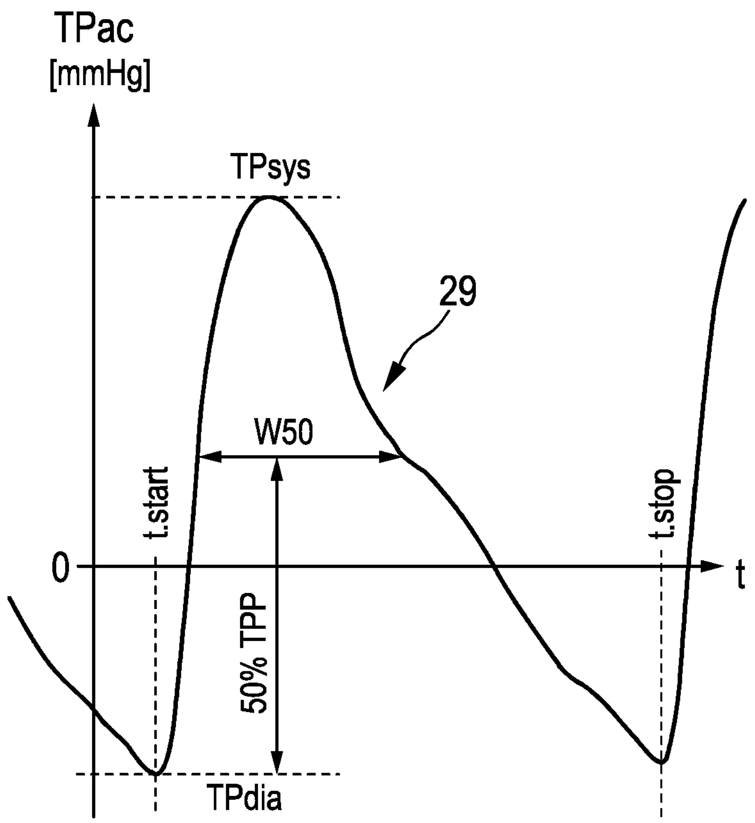

The control device 3 can also be adapted to determine the entire pulse area (TPA) of the respective pulse 29 being the entire area under the respective pulse curve within the time defined by t.start to t.stop and ranging from the feature determination pulse's pressure at an end-diastolic point (TPdia) to a feature determination pulse's maximum systolic pressure (TPsys). Preferentially, the entire pulse area TPA is scaled to TPP=1 as indicated in FIG. 7. This scaled pressure pulse area is named "TPA.norm". The control device 3 can also be adapted to determine the pulse width at half maximum (W50) of the respective pulse 29 as indicated in FIG. 8.

Figure 9:
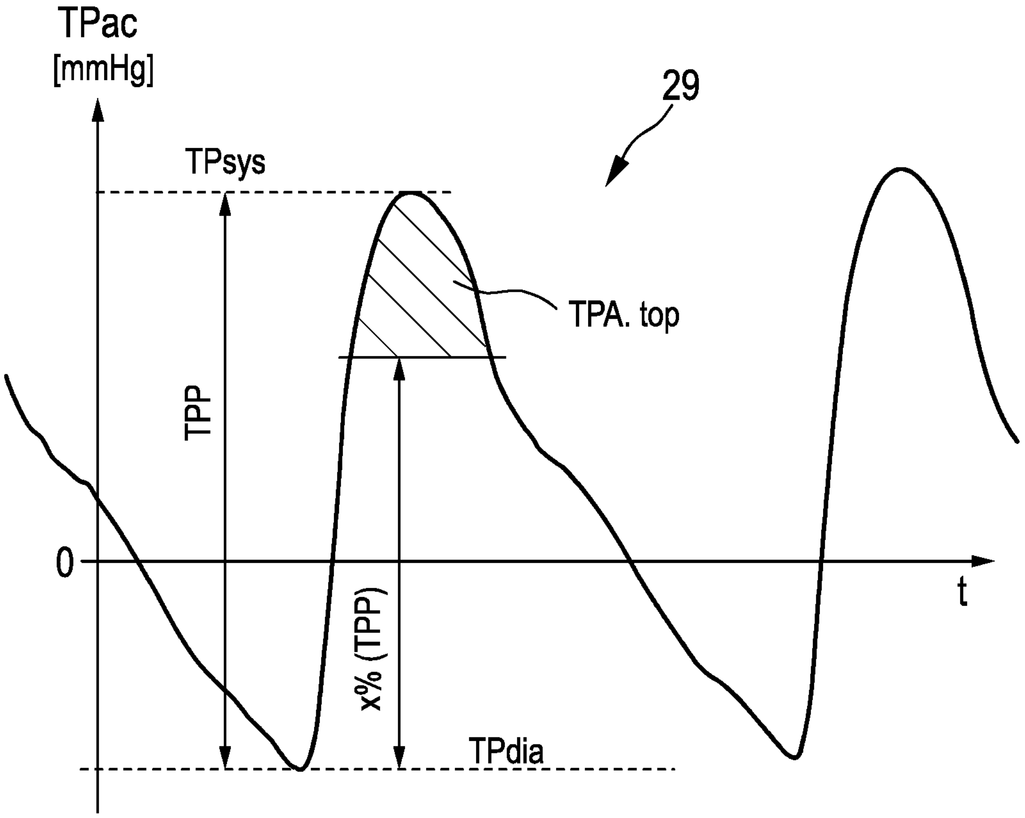

Moreover, the control device 3 can be adapted to determine the pulse area (TPA.top) of the respective pulse 29 being the upper area under the respective pulse curve as indicated in FIG. 9. The lower border of the upper pulse area TPA.top is defined by a predefined percentage of the difference TPP. The percentage value can be determined, for instance, as described below with reference to the determination of the predefined exponents during an initial training phase, in which the percentage value, exponents and further parameters are determined such that a difference between a) a non-invasive blood pressure value, which is determined by using the present method, and b) an invasively measured blood pressure value is minimized. For more details regarding the features, particularly the upper pulse area TPA.top, reference is made to DE 10 2017 110 770 B3.

FIGS. 6 to 9 show a TPac pulse curve such that in this example also the features, i.e. the TPW_parameters, have been defined based on the TPac pulse curve. However, as mentioned above, it is also possible to define these or other features based on a TP pulse curve.

The control device 3 is further configured to, in the first measurement time period $T_1$, determine for a respective pressure pulse a start value TPWP_F, to be used for determining the start of the second measurement time period, based on the several features, which have been determined for the respective pressure pulse, such that for several pressure pulses, which are present at different times, several start values TPWP_F are determined. In particular, the control device 3 is configured to determine during the first measurement time period $T_1$ for a respective pressure pulse a start value TPWP_F by exponentiating the features with predetermined exponents and by multiplying the exponentiated features which each other. This will be explained further below.

The control device 3 is further configured to, in the first measurement time period $T_1$, form a start curve TPW_F-curve, to be used for determining the start of the second measurement time period $T_2$, based on the several start values TPWP_F, and control, after the start curve TPW_F-curve has reached a first maximum, the measurement system 1 such that the second measurement time period $T_2$ succeeds. The start curve TPW_F-curve is preferentially formed based on the several start values TPWP_F by low pass filtering the several start values TPWP_F. The low pass filtering is preferentially a moving average filtering, wherein the filter window can have a length of, for instance, 4 s. The filter window is preferentially centered at the time, for which currently an average value is to be determined.

In particular, the control device 3 can be configured to determine, for each pressure pulse in the first measurement time period $T_1$, a start value TPWP_F by combining at least two of the features which have been determined for the respective pressure pulse. In particular, the control device 3 can be configured to multiply a) the determined pulse area TPA.norm to the power of a predetermined first exponent (exp1) with b) the determined difference TPP to the power of a predetermined second exponent (exp2). Thus, a start value TPWP_F can be calculated in accordance with following equation:

with predetermined exp1≠0, exp2≠0.

The control device 3 can also be configured to determine a start value TPWP_F by dividing a) the determined pulse area TPA.norm to the power of a predetermined third exponent (exp3) by b) the determined pulse duration t(pulse) to the power of a predetermined fourth exponent (exp4) and multiplying the resulting quotient with c) the determined difference TPP to the power of a predetermined fifth exponent (exp5). This can be expressed by following equation:

$$\text{TPWP\_F}=\text{TPA.norm}^{exp3}/t(\text{Pulse})^{exp4}\cdot TPP^{exp5} \tag{2}$$

with predetermined exp3≠0, exp4≠0, exp5≠0.

The control device 3 can also be configured to determine a start value for a respective pressure pulse based on multiplying the calculation result as obtained by using, for instance, equation (1) or equation (2), with the width at half maximum (W50) to the power of a further predetermined exponent. For instance, if equation (2) is multiplied by the width at half-maximum W50, the following equation (3) results:

$$\text{TPWP\_F}=\text{TPA.norm}^{exp6}/t(\text{Pulse})^{exP7}\cdot TPP^{exp8}\cdot W50^{exp9} \tag{3}$$

with predetermined exp6≠0, exp7≠0, exp8≠0, exp9≠0.

Thus, in this embodiment based on at least TPP and TPA.norm for a respective pulse curve a TPWP_F can be calculated that reflects a characteristic value for the respective pulse curve by combining and weighting the amplitude and area parameters, wherein any of the TPWP_F can be extended by multiplying with W50 to the power of a respective exponent. The exponents for the different equations are predetermined, preferentially in the way that will be explained further below.

The determined start values TPWP_F are used for forming the start curve TPWP_F in the first measurement time period $T_1$. However, as shown in FIG. 5, the start values TPWP_F and hence the start curve TPWP_F-curve can also be determined for the second measurement time period $T_2$.

The control device 3 is further configured to, in the first measurement time period $T_1$, determine a first blood pressure value based on the start curve TPW_F-curve, determine the second slope based on the determined first blood pressure value and control, after the start curve TPW_F-curve has reached a first maximum, the measurement system 1 such that the second measurement time period $T_2$ succeeds with the determined second slope. The first blood pressure value is preferentially the systolic arterial blood pressure value (SAPni). The control device 3 is further configured to determine a final blood pressure value based on the pressure TP measured in the second measurement time period $T_2$.

The control device 3 is further configured to determine a respiration rate value RR being indicative of the respiration rate based on the pressure TP measured in the second measurement time period or to receive the respiration rate value RR from another device. In particular, the control device 3 can be configured to determine the respiration rate value RR online, i.e. while still measuring the pressure TP in the second measurement time period. Moreover, the other device could be, for instance, a ventilator machine providing the respiration rate value to the control device. Moreover, the control device 3 is preferentially configured to stop the second measurement time period as soon as the respiration rate value RR indicates that the second measurement time period covers 3.5 respiration or ventilation cycles and/or a predetermined maximum measurement time period has been reached and/or a maximum mean pressure value has been reached. The predetermined maximum measurement time period preferentially corresponds to 3.5 times an expected maximal respiration or ventilation cycle duration. This expected maximal respiration or ventilation cycle duration could be, for instance, 7.5 s which corresponds to a respiration rate value RR of 8 respiration or ventilation cycles per minute. The maximum mean pressure value is preferentially larger than the systolic arterial blood pressure. It is especially the systolic arterial blood pressure plus 20 mmHg. The systolic arterial blood pressure is here preferentially the first blood pressure value or a blood pressure value which is determined based on the pulses measured during the second measurement time period, wherein in the latter case the maximum mean pressure value is modified during the second measurement time period.

The control device 3 can be configured to modify the second slope based on the respiration rate value RR determined during the second measurement time period and/or depending on the maximum mean pressure value. Thus, if the maximum mean pressure value changes during the second measurement time period, because it is, for instance, the systolic arterial blood pressure plus 20 mmHg and because the systolic arterial blood pressure is measured during the second time period, the second slope can change depending on the respiration rate value and the systolic arterial blood pressure measured during the second measurement time period.

In order to determine the blood pressure value based on pressure measured in the second measurement time period $T_2$, the control device 3 is configured to determine, for a respective pressure pulse measured in the second measurement time period $T_2$, a blood pressure determination value TPWP_S based on a combination of at least two of the determined features such that for several pressure pulses, which are present at different times, several blood pressure determination values TPWP_S are determined, wherein the several blood pressure determination values TPWP_S determined for the several pressure pulses and hence for several times form a blood pressure determination curve TPW_S-curve.

Thus, several features can be determined for a respective pressure pulse measured in the second measurement time period T2, wherein a blood pressure determination value TPWP_S can be determined by combining at least two of the determined features such that for several pressure pulses, which are present at different times, several blood pressure determination values TPWP_S are determined, wherein the several blood pressure determination values TPWP_S determined for the several pressure pulses and hence for several times form the blood pressure determination curve TPW_S-curve.

The control device 3 is configured such that the forming of the blood pressure determination curve TPW_S-curve based on the several blood pressure determination values TPWP_S includes a low pass filtering of the several blood pressure determination values TPWP_S. Also here the low pass filtering is preferentially a moving average filtering, which is preferentially centered at the time for which currently an average value is to be determined.

In particular, the control device 3 is configured such that the low pass filtering of the several start values TPWP_F and the low pass filtering of the several blood pressure determination values TPWP_S both use a filtering window, wherein the filtering window for low pass filtering the several start values TPWP_F has a window length being smaller than a window length of the filtering window for low pass filtering the several blood pressure determination values TPWP_S. For instance, the window length for low pass filtering the several blood pressure determination values TPWP_S could be twice the window length for low pass filtering the several start values TPWP_F. In an embodiment the window length for low pass filtering the several blood pressure determination values TPWP_S is 8 s and the window length for low pass filtering the several start values TPWP_F is 4 s. Moreover, in an embodiment the several blood pressure determination values TPWP_S are low pass filtered several times, preferentially twice, whereas the several start values TPWP_F might be low pass filtered only one time. This leads to a stronger low pass filtering of the measurements obtained in the second measurement time period $T_2$ in comparison to the filtering of the measurements obtained in the first measurement time period $T_1$, which in turn allows for a more accurate determination of the blood pressure based on the blood pressure determination curve TPW_S-curve. The low pass filtering is preferentially carried out such that heart lung interactions are eliminated in the blood pressure determination curve TPW_S-curve, in order to allow for the high quality blood pressure determination. For the start curve the elimination of the heart lung interactions is not necessarily required, because a rough estimation of the blood pressure and the ability to detect a maximum of the start curve TPW__F-curve are sufficient. In an embodiment heart lung interactions detectable on the start curve are even used in the second measurement time period for determining the respiration rate value RR. Thus, the start curve TPW__F-curve might also be determined during the second measurement time period based on the pressure pulses measured in the second measurement time period as shown in FIG. 5.

In an embodiment the blood pressure determination curve TPW_S-curve is determined as explained in WO 2018/210931 A1. Particularly determining the arterial blood pressure based on the determined maximum of the blood pressure determination curve and depending on the exerted pressure on the skin, i.e. tissue pressure, allows a relatively short measurement time. Generally, the tissue pressure is dependent on the height of arterial blood pressure, of arterial pulse pressure, and the inverse of the heart rate.

As described in WO 2018/210931 A1, in an embodiment the control device 3 is configured to determine the TPcl value at the time point at which the blood pressure determination curve TPW_S-curve has its maximum (TPW_S-curve.max), wherein the TPcl value at the time of this maximum may be denoted as "TPcl@TPW_S-curve.max". The control device 3 is further configured to determine a lower envelope of the tissue pressure TP by applying a filter to the end-diastolic points of the tissue pressure TP. The filter can be same as the filter used for determining, for instance, the blood pressure determination curve TPW_S-curve. The resulting curve can be named "TPdia-curve". Moreover, the control device 3 can be configured to determine an upper envelope of the tissue pressure TP by applying a filter to the systolic maxima of the tissue pressure TP. In addition, this filter can be similar to the filter used for, for instance, generating the blood pressure determination curve TPW_S-curve. This curve can be named "TPsys-curve". The control device 3 can then be configured to determine the systolic arterial pressure value as a predetermined percentage (TPcl.s%) of TPcl@TPW_S-curve.max. This predetermined percentage is preferentially within a range from 100 to 150 percent, further preferred from 110 to 150 percent. The noninvasive systolic arterial pressure may be named "SAPni" and the predetermined percentage may be denoted as "TPcl.s%(TPcl@TPW_S-curve.max)".

The control device 3 can also be adapted to determine the noninvasive systolic arterial pressure SAPni as a predetermined percentage (TPsys.s%) of the Tpsys-curve at the temporal position at which the blood pressure determination curve TPW_S-curve has its maximum. This predetermined percentage is preferentially within a range from 100 to 140 percent.

The control device 3 can be configured to determine the noninvasive mean arterial pressure (MAPni) as the TPcl value or alternatively the value of the TPdia-curve or alternatively the value of the TPsys-curve at a time point t(bx) being the time point at which the blood pressure determination curve TPW_S-curve has a value bx representing a predetermined percentage relative to its maximum. The control device 3 can also be adapted to alternatively determine the noninvasive mean arterial pressure MAPni as a predetermined percentage (TPcl.m%) of TPcl at TPW_S-curve.max, wherein the predetermined percentage is preferentially within a range from 80 to 110 percent.

The control device 3 can also be configured to determine the noninvasive diastolic arterial pressure DAPni as the value of the TPdia-curve or alternatively of the TPcl curve at a time point t(cx) being the time point at which the blood pressure determination curve TPW_S-curve has a value cx representing a predetermined percentage of its maximum. The control device 3 can also be configured to alternatively determine DAPni as a predefined percentage (TPcl.d%) of TPcl@TPW_S-curve.max, wherein this predetermined percentage is preferentially within a range from 60 to 80 percent. Preferentially, the control device 3 is configured to determine the first blood pressure value based on the start curve TPW_F-curve in the same way, i.e. as described above with respect to the TPW_S-curve, wherein it is possible to use for the determination of the first blood pressure value based on the TPW_F-curve parameters like the percentage values which differ from the parameters used for determining the blood pressure value based on the TPW_S-curve. Also the parameters for the determination of the first blood pressure value based on the start curve TPW_F-curve can be predetermined by calibration.

As explained above, the exponents used for determining the start curve TPW_F-curve and for determining the blood pressure determination curve TPW_S-curve are determined by calibration. Also the percentages used for determining the blood pressure values are determined by calibration. Thus, these parameters are predetermined such that, during a calibration phase, deviations between very accurately measured invasive blood pressure values and the blood pressure values obtained by the measurement system are minimized and the time needed for a blood pressure measurement is relatively low.

The values TPcl.s%, TPsys.s%, TPcl.m%, TPcl.d%, bx, cx are preferentially calibrated as described in WO 2018/210931 A1 by statistically evaluation of a calibration set consisting of measurement pairs of simultaneously recorded invasive blood pressure values and noninvasive blood pressure values from an adequate number of individuals in different hemodynamic conditions. The noninvasive blood pressure values are determined as described above by the measurement system 1 and the parameters like the values TPcl.s%, TPsys.s%, TPcl.m%, TPcl.d% can be optimized such that deviations between invasive blood pressure values and noninvasive blood pressure values are minimized.

The control device 3, particularly the processor 11 of the control device 3, can be adapted to estimate a kind of blood pressure value based on two other already measured kinds of blood pressure values. In particular, one of the blood pressure values MAPni, SAPni and DAPni can be estimated based on the other of these blood pressure values. This may be done in accordance with following equations:

$$\text{SAPni}=c1\cdot\text{MAPni}+c2\cdot(\text{MAPni}-\text{DAPni})-c3\ \text{mmHg} \quad (4)$$

with c1=(0.2 . . . 0.7), c2=(2 . . . 6), c3=(−5 . . . 5), $$\text{MAPni}=c4\cdot\text{DAPni}+c5\cdot(\text{SAPni-DAPni})-c6\ \text{mmHg} \quad (5)$$

with c4=(0.8 . . . 1.3), c5=(0.25 . . . 0.5), c6=(−5 . . . 5), $$\text{DAPni}=c7\cdot\text{MAPni}-c8\cdot(\text{SAPni-MAPni})-c9\ \text{mmHg} \quad (6)$$

with c7=(0.6 . . . 1.1), c8=(0.15 . . . 0.4), c9=(−5 . . . 5).

The coefficients and constants of equations (4), (5) and (6) are predetermined by calibration based on a statistical evaluation of an as large as possible and adequately widely spread set of clinical invasive blood pressure data. Thus, very accurate invasive blood pressure values SAPi (invasive systolic arterial pressure), MAPi (invasive mean arterial pressure) and DAPi (invasive diastolic arterial pressure) are used, wherein, given these very accurate invasive blood pressure values, the coefficients and constants of the equations (4), (5) and (6) are modified such that these equations are valid.

The blood pressure measurement is intended to be used in a sequence of measurements in rapid succession to allow for an effective semi-continuous blood pressure monitoring such that the stress for the monitored individual, i.e. for the monitored subject, is minimized. This sequence of fast pressure measurements can also be regarded as being a noninvasive fast mode cycle measurement of the blood pressure.

The control device 3 can be configured to determine a blood pressure determination value TPWP_S for a respective pressure pulse based on multiplying a) the determined area TPA or TPA.norm to the power of a predetermined tenth exponent (exp10) with b) the determined difference TPP to the power of a predetermined eleventh exponent (exp11). For instance, for the respective pressure pulse a blood pressure determination value TPWP_S can be calculated in accordance with following equation:

$$\text{TRWP\_S}=\text{TPA.norm}^{exp10}\cdot\text{TPP}^{exp11} \quad (7)$$

with predetermined exp 10≠0, exp11≠0.

The control device 3 can also be configured to determine a blood pressure determination value TPWP_S for a respective pressure pulse by dividing a) the determined area TPA or TPA.norm to the power of a predetermined twelfth exponent (exp12) by b) the determined duration (t(Pulse)) to the power of a predetermined thirteenth exponent (exp13) and multiplying the resulting quotient with c) the determined difference TPP to the power of a predetermined fourteenth exponent (exp14). For instance, a blood pressure determination value TPWP_S can be calculated in accordance with following equation:

$$\text{TPWP\_S}=\text{TPA.norm}^{exp12}/t(\text{Pulse})^{exp13}\cdot\text{TPP}^{exp14} \quad (8)$$

with predetermined exp12≠0, exp13≠0, exp14≠0.

The control device 3 can also be configured to determine a blood pressure determination combination value TPWP_S for a respective pressure pulse by further multiplying with the width at half-maximum W50 to the power of a further predetermined exponent. For instance, a blood pressure determination combination value TPWP_S can be calculated in accordance with following equation:

$$TPWP\_S=TPA.norm^{exp15}/t(Pulse)^{exp16}\cdot TPP^{exp17}\cdot W50^{exp18} \quad (9)$$

with predetermined exp15≠0, exp 16≠0, exp17≠0, exp18≠0.

The control device 3 is configured to determine the blood pressure based on the blood pressure determination curve TPW_S-curve. Preferentially, the control device 3 is configured 3 to determine a maximum of the blood pressure determination curve TPW_S-curve and to determine the blood pressure based on the determined maximum and the measured pressure.

The different exponents are preferentially predefined and can be predetermined by calibration measurements, wherein by invasive means reference blood pressure values are determined very accurately and the exponents are determined such that the measurement system controlled by the control device yields the very accurately invasively measured blood pressure values with high statistical precision and accuracy. In particular, for the calibration measurement pairs of simultaneously recorded invasive and noninvasive blood pressure values from an adequate number of individuals in different hemodynamic conditions are used. It should be noted that the calibration is preferentially only carried out in a development phase, i.e. not during an actual blood measurement procedure. The calibration can be carried out separately for different shell sizes, i.e. preferentially for different blood pressure cuff sizes, or for different groups of shell sizes. For instance, for different shell sizes or groups of shell sizes, different sets of exponents can be determined by calibration, i.e. for each shell size or for each group of shell sizes a respective set of exponents can be determined.

The control device 3 is configured to further determine a hemodynamic monitoring parameter based on the pressure measured in the second measurement time period $T_2$. In particular, the control device 3 is configured to determine, as the hemodynamic monitoring parameter, at least one of a fluid responsiveness parameter FRP, a cardiac output CO, a systemic arterial resistance SAR, and a cardiac power output CPO. As a fluid responsiveness parameter FRP, a pulse pressure variation PPV, a systolic pressure variation SPV or a stroke volume variation SPV may be determined based on the pressure measured in the second measurement time period $T_2$. For determining one or several hemodynamic monitoring parameters, i.e. one or several hemodynamic parameters, based on the pressure measured in the second measurement time period $T_2$ known algorithms can be used like the algorithms disclosed in EP 2 759 257 B1 and WO 2019/211210 A1 which are herewith incorporated by reference.

As explained above, for determining the start curve TPW_F-curve, the blood pressure determination curve TPW_S-curve and the envelope curves TPsys-curve and TPdia-curve a filter is used. Moreover, also for determining TPcl based on TP a filter is used. As the filter preferentially a low pass filter is used. The low pass filter can be, for instance, a cascaded moving average filter with a varying window length of up to 8 s, wherein the window length can be shorter at the beginning and at the end of the filtering, in order to a minimize filter settling time. For instance, the filtering can include averaging within a moving window containing signals of at least three TP pressure pulse curves and maximal 8 s, and applying the moving average filtering twice (2×8 s filter). Optionally, a signal padding can be applied before the beginning and/or after the end of the signal for fully filling the filter windows before filtering. For instance, padding with the first pressure pulse's value before the beginning and the last pressure pulse's value after the end can be applied.

In an embodiment, due to the filter delay TPcl is extrapolated from its previous values to be available for the last part of the measured signal. The filter can be applied to, for instance, extract TPcl from TP, form a smooth TPW_F-curve and a smooth TPW_S-curve without variation caused by blood pressure pulsation and to create an envelope function over systolic peaks (TPsys-curve) and over end-diastolic minima (TPdia-curve) of TP. However, the smoothing is preferentially such that the TPW_F-curve still shows heart lung interactions.

In an embodiment, for defining the blood pressure determination curve TPW_S-curve, equation (8) is used with following exponents exp12=0.7, exp 13=0.4 and exp14=1.0. By using these exponents together with equation (8) a very good precision and accuracy could be obtained for the blood pressure values as validated with statistical evaluation of noninvasive blood pressure values as determined by the measurement system 1 versus simultaneously taken invasive blood pressure reference values, particularly for inflation-deflation time periods within a range from 20 to 60 seconds. The following set of exponents together with equation (7) leads to an even higher precision and accuracy, but leads also to a few seconds longer measurement time: exp 10=1.0, exp11=1.21. In an embodiment, for determining the start curve TPW_F-curve, equation (2) is used together with following exponents: exp3=1.1, exp4=0.4, exp5=0.5.

Figure 10:
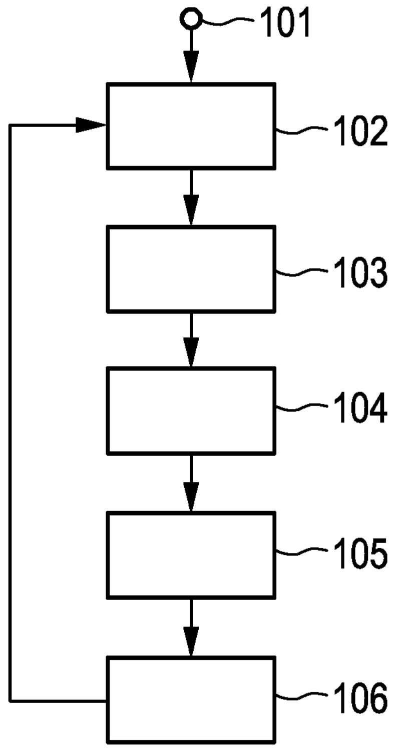
FIG. 10 shows a flowchart exemplary illustrating an embodiment of a control method for controlling the measurement system for measuring blood pressure of a subject.

In the following an embodiment of a control method for controlling the measurement system 1 will be exemplary described with reference to a flowchart shown in FIG. 10.

After initializing and starting the system in step 101, in step 102 the pressure applicator 6, 8 increases the applied pressure over time in the zeroth measurement time period $T_0$ with a zeroth slope. During the zeroth measurement time period $T_0$ the pressure sensor 7 measures the pressure TP on the skin, wherein the measured pressure TP comprises several pressure pulses. Moreover, still in step 102, a heart rate value HR being indicative of the heart rate of the subject is determined based on the at least one pressure pulse of the pressure TP measured in the zeroth measurement time period $T_0$ and, after the determination of the heart rate value HR, a first slope is determined based on the determined heart rate value HR. In particular, after two subsequent pressure pulses have been detected and used for determining the heart rate value HR, in step 103 the first measurement time period $T_1$ succeeds with the determined first slope.

In step 103, in the first measurement time period $T_1$, for each pressure pulse of at least some of the plurality of pressure pulses, several features, which characterize the respective pressure pulse, are determined and for a respective pressure pulse a start value TPWP_F is determined, to be used for determining the start of the second measurement time period $T_2$, based on a combination of at least two of the features, which have been determined for the respective pressure pulse, such that for several pressure pulses, which are present at different times, several start values TPWP_F are determined. Moreover, still in step 103, a start curve TPW__F-curve is formed, to be used for determining the start of the second measurement time period $T_2$, based on the several start values TPWP_F, wherein, after the start curve TPW_F-curve has reached a first maximum, the second measurement time period $T_2$ succeeds.

In step 104 the second measurement time period $T_2$ is carried out, wherein based on the pressure measured in the second measurement time period a blood pressure value is determined.

After the second measurement time period $T_2$, in step 105 the cuff is deflated. After deflation and a pause for allowing venous return in step 106, the method continues with step 102. Thus, the control method can be carried out in a loop for continuously monitoring the blood pressure over time in several measurement cycles. While carrying out steps 102 to 105, the control device calculates the blood pressure value in parallel. The loop can be carried out until an abort criterion is fulfilled. For instance, the monitoring of the blood pressure is interrupted, if a physician has inputted a corresponding command into the measurement system via an input unit like a keyboard, a computer mouse, a touchpad, et cetera.

The measurement system 1 provides a heart rate value HR and non-invasive blood pressure niBP adaptive method to shorten measurement time with a high-fidelity oscillometry blood pressure cuff, which leads to less strain on the measurement extremity and less stress to the patient. The time-optimized adaptive clamping pressure control is divided into three sections, i.e. a zeroth measurement time period To which preferentially provides a maximum fast pre-inflation, a first measurement time period $T_1$ which preferentially provides a heart rate value HR dependent fast inflation and a second measurement time period $T_2$ which preferentially provides an niBP dependent slow inflation.

The measurement system can be adapted such that the measurement starts with a maximum possible TPcl increase rate that allows a detection of at least two subsequent pressure pulses TP below TPcl=MAP. For instance, in this zeroth measurement time period To the increase rate, i.e. the zeroth slope, can be 8 mmHg/s. The control device can then be configured to determine the heart rate value HR as soon as two subsequent pressure pulses TP have been detected. Then, it can be switched to the first measurement time period $T_1$ in which a heart rate value HR dependent TPcl increase rate is preferentially used. This increase rate, i.e. the first slope, can be, for instance, 4 mmHg/PW, wherein PW indicates the width of the respective pulse. The measurement during the first measurement time period $T_1$ is carried out such that enough pressure pulses TP are collected, which allow to provide a first estimate of a blood pressure value niBP, wherein TPcl might be near by MAP. In particular, in the first measurement time period $T_1$ a fast tissue pressure waveform curve TPW_F-curve is recorded, i.e. a start determination curve TPW_F-curve is recorded, based on the start values TPWP_F which are determined depending on features of the pressure pulses and statistically predetermined exponents. The start values TPWP_F are filtered by using, for instance, a moving average filter with a window length of 4 s which leads to a 2 s filter delay. The window length is preferentially chosen such that a good balance is achieved between a minimal filter delay and an acceptable accuracy of a first estimation of the blood pressure value niBP which is used for the further inflation control. As can be seen in FIG. 5, the filtering, i.e. the smoothing, can be carried out such that heart-lung interactions are still visible in the finally resulting TPW__F-curve.

After the first maximum of the TPW_F-curve has been detected, the first blood pressure value niBP estimate can be calculated based on the TPW_F-curve as described above with reference to the TPW_S-curve. The TPWP_F-curve can be formed based on the TPWP_F values as defined, for instance, by equations (1), (2) or (3). However, the TPWP_F values can also be determined by using another combination of features which are exponentiated. For instance, the TPWP_F values can be determined in accordance with the determination of the TPWP_S values as described, for instance, in equations (4), (5) or (6). It is also possible to determine the TPWP_S values and/or the TPW_F values in accordance with following equation:

$$TFWP=TPA.top^{exp9}/t(Pulse)^{exp20}\cdot TTP^{exp21}\cdot W50^{exp22} \quad (10).$$

The TPWP_F and TPW_S values can also be determined in accordance with following equation:

$$TPWP=TPA.top.norm^{exp23}/t(Pulse)^{exp24}\cdot TPP^{exp25}\cdot W50^{exp26} \quad (11).$$

The feature TPA.top.norm is the area TPA.top normalized to TPP. The exponents in equations (10) and (11) are determined, as described above, by calibration.

Equations (1), (2) and (3) can be preferred, if MAPni, i.e. the non-invasive mean arterial pressure, should be determined, because TPA.norm is relatively sensitive to waveform changes, i.e. to pressure pulse changes, at the lower TP pulse area occurring while TPcl is crossing the mean arterial pressure. Equations (10) and (11) can be more preferred, if SAPni, i.e. the non-invasive systolic arterial pressure, should be determined, because TPA.top and TPA.top.norm are more sensitive to TP pulse wave changes near TPsys at TPcl near by SAP. It is also possible to determine the TPWP-F and/or the TPWP-S values in accordance with following equation:

$$TPWP=TPA.top^{exp27}\cdot TPA.top.norm^{exp28}\cdot TPA.norm^{ex29}/t(Pulse)^{exp30}\cdot TPP^{exp31}\cdot W50^{exp32} \quad (12).$$

Also the exponents for equation (12) can be obtained by calibration, wherein in equation (12) and also in the other equations it is possible to use different sets of exponents depending on whether, for instance, SAPni or MAPni should be determined. It is also possible to determine several niBP values in different ways and to then weightedly combine these niBP values. For instance, a DAPni value can be determined based on a TPW-curve, i.e. based on the TPW_F-curve and/or the TPW_S-curve, and this DAPni value can be weightedly combined with a further DAPni value, which has been determined based on an estimation formula like equation (6). It is also possible to determine several TPW-curves, i.e., for instance, several TPW_S-curves, by using different combinations of the determined features as described in the above equations, to determine for each TPW-curve a respective blood pressure value like an SAPni or MAPni value and to weightedly combine the several blood pressure values determined for the several TPW-curves. The weighted combination of the several blood pressure values can be, for instance, a simple averaging.

After the first maximum of the TPW_F-curve has been detected and the first blood pressure value has been determined based on the TPW_F-curve like a first SAPni value, the second measurement time period $T_2$ starts with a slower TPcl increase rate, i.e.

with a second slope being smaller than the first slope. The second slope is preferentially chosen such that it allows recording at least 3.5 ventilation or respiration cycles until TPcl=SAPni+20 mmHg for calculating a fluid responsive parameter FRP. Depending on the degree of fluid responsiveness, a respiration rate RR may already be detectable online during the measurement as in FIG. 5 by using a TPWP_value, i.e. a combination of features, which is sensitive to the hard-lung interactions. In an embodiment the second measurement time period $T_2$ can then be terminated as soon as 3.5 respiration or ventilation cycles have been identified. Otherwise, the second slope may be set according to a maximally expected ventilation or respiration cycle duration of 7.5 s which corresponds to a respiration rate of 8/min.

In the second measurement time period $T_2$ the relatively slow TPW_S-curve is recorded for a more accurate niBP estimation in comparison to the niBP estimation made based on the pressure measured in the first measurement time period $T_1$. The TPWP_S values are filtered by using, for instance, an adaptive moving average over two windows, each up to 8 s, wherein the window length of the averaging windows is preferentially longer in comparison to the window length used for the TPWP_F values. In particular, the filtering, i.e. the smoothing, of the TPWP_S values is such that heart-lung interactions are eliminated, whereas the filtering of the TPW_F values is such that the heart-lung interactions might still be visible as illustrated in FIG. 5. Correspondingly the TPW_S-curve does not show any heart-lung interactions anymore, which contributes to the more accurate final blood pressure measurement.

While measuring the pressure in the second measurement time period $T_2$, the second slope can be continuously adjusted based on blood pressure values determined during the second measurement time period $T_2$, which are determined based on the TPW_S-curve formed during the measurement. The second slope can also continuously be modified based on an online detected respiration rate which might be obtained from another device or which might be obtained from the heart-lung interactions visible in the TPW_F-curve also formed during the second measurement time period $T_2$.

After the second measurement time period $T_2$ has been stopped, a final non-invasive blood pressure value and also advanced hemodynamic monitoring parameters can be determined. For instance, the control device can be configured to determine as the hemodynamic monitoring parameter at least one of a fluid responsiveness parameter (FRP), a cardiac output (CO), a systemic arterial resistance (SAR) and a cardiac power output (CPO). The control device can be adapted to determine, as a fluid responsiveness parameter (FRP), for instance, a pulse pressure variation (PPV), a systolic pressure variation (SPV) or a stroke volume variation (SPV) based on the pressure measured in the second measurement time period. The cardiac power output CPO might be determined by multiplying the mean arterial pressure with the cardiac output CO.

Figure 11:
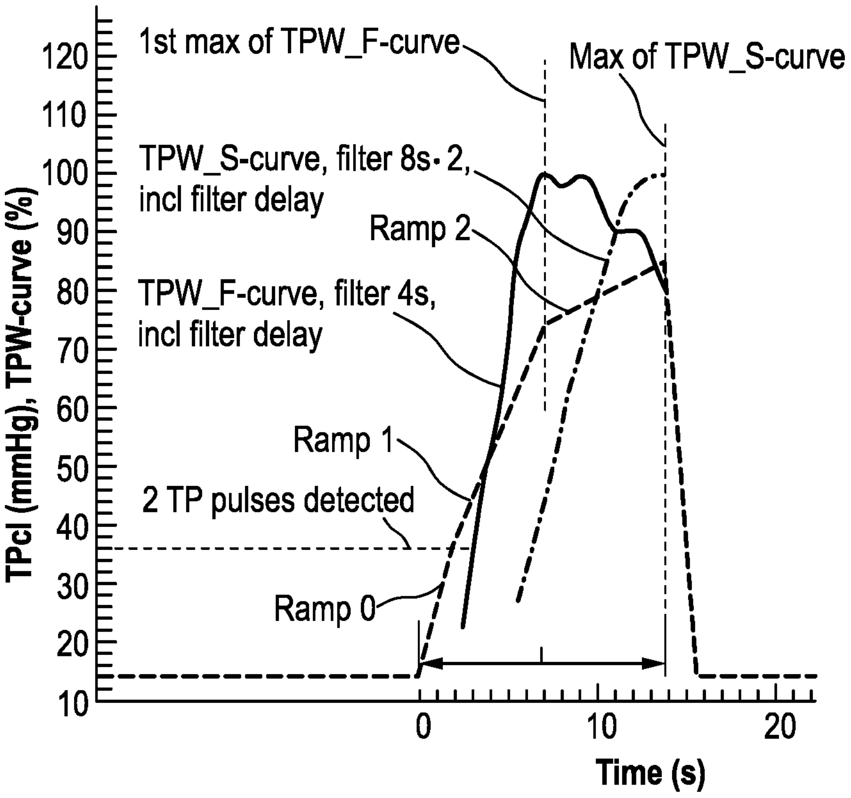
FIG. 11 shows schematically and exemplary a measured tissue pressure and further values derived from the tissue pressure measurement in accordance with a further embodiment of the invention.

In a further embodiment the control device 3 is configured such that the second measurement time period ends, after the TPW_S-curve has reached its maximum as schematically and exemplarily illustrated in FIG. 11. This is especially preferred, if no FRPs are required. This is also preferred if only blood pressure values should be determined. The cycle time can then be reduced which also reduces the maximally necessary TPcl to a level below SAP. The perfusion is therefore never completely interrupted at the measurement site of the subject. Moreover, the measurement time is remarkably shortened, which causes less physical stress to the subject. This is important for long-time monitoring, especially in, for instance, septic patients which skin alterations. After the maximum of the TPW_S-curve has been detected, the blood pressure value like SAPni or DAPni can be determined as described above based on the maximum of the TPW_S-curve. It is also possible to determine the parameters SV, CO, SAR and CPO as also described above.

Although in above described embodiments the features are determined by using the TPac pulses, the features can also be determined by using directly the measured pressure pulses, i.e. the TP pulses. It is also possible to process the TP pulses in another way, i.e. not by subtracting the mean TP value for determining the TPac pulses. For instance, for the respective measured pressure pulse the pressure values at t.start and t.stop can be connected by a straight line and this straight line can be subtracted from the respective measured pressure pulse, in order to determine a features determination pulse.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the determination of features of pulses, of certain curves, of blood pressure values, et cetera performed by one or several units or devices can be performed by any other number of units or devices. The calculations and/or the control of the measurement systems in accordance with the control method can be implemented as program code means of a computer and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope. In particular, the letters like TPP, TPA, et cetera used in brackets in the claims as reference signs should not be construed as limiting the scope. For instance, also other features than the features, which are represented by the reference signs, can be used in accordance with the claims.

The invention relates to a control device for controlling a measurement system for measuring blood pressure and optionally hemodynamic parameters of a subject. In a first measurement time period, for measured pressure pulses, features are determined, which characterize the respective pressure pulse. Based on the features, start values are determined and, based on the start values, a start curve TPW_F-curve is formed. The measurement system is controlled such that, after the start curve has reached a first maximum, a second measurement time period succeeds, wherein a blood pressure value is determined based on the pressure measured in the second measurement time period. It has been found that by using the maximum in the first measurement time period for defining a start point for the actual blood pressure measurement, a blood pressure value and optionally also hemodynamic parameters of a subject can be determined very accurately and fast.

The invention claimed is:

1. A controller, including at least one processor, for controlling a measurement system for measuring blood pressure of a subject, wherein the measurement system comprises a) a shell for encasing a part of the subject, through which blood flows, b) a pressure applicator configured to apply, from outside the shell, pressure to the shell and thereby to the encased part of the subject, and c) a pressure sensor for measuring the tissue pressure (TP) on the skin of the encased part of the subject, wherein the controller is configured to:

control the measurement system such that the pressure applicator increases the applied pressure over time in a first measurement time period (T.sub.1) with a first slope and in a second measurement time period (T.sub.2) with a second slope, wherein T.sub.1 and T.sub.2 are temporally arranged in this sequence, and the pressure sensor measures TP on the skin during the first and second measurement time periods, wherein TP comprises a plurality of pressure pulses, determine, in T.sub.1, for each pressure pulse of at least some of the plurality of pressure pulses, at least one feature (TPP, t(Pulse), TPA, TPA.norm, W50, TPA.top, TPA.top.norm), which characterizes the respective pressure pulse, wherein TPP denotes the difference between a respective pressure pulse's maximum systolic pressure (TPsys) and the respective pressure pulse's pressure at the end-diastolic point (TPdia), t(Pulse) denotes the duration of the respective pressure pulse, TPA denotes the entire area of the respective pressure pulse, TPA.norm denotes a normalized area of the respective pressure pulse, W50 denotes the width at half maximum of the respective pressure pulse, TPA.top denotes an upper area under an upper part of the respective pressure pulse, and TPA.top.norm denotes a normalized upper area under an upper part of the respective pressure pulse;

determine for each of the at least some of the plurality of pressure pulses, a start value (TPWP_F), to be used for determining the start of the second measurement time period, based on the at least one feature (TPP, t(Pulse), TPA, TPA.norm, W50, TPA.top, TPA.top.norm), which has been determined for the respective pressure pulse, such that for several pressure pulses which are present at different times, several start values (TPWP_F) are determined, form a start curve (TPW_F-curve), to be used for determining the start of the second measurement time period, based on the several start values (TPWP_F), and control, after the TPW_F-curve has reached a first maximum, the measurement system such that the second measurement time period succeeds, determine a blood pressure value (niBP) based on the TP measured in T.sub.2, determine, in T.sub.1, a first blood pressure value based on the TPW_F-curve, determine the second slope based on the determined first blood pressure value and control, after the TPW_F-curve has reached the first maximum, the measurement system such that T.sub.2 succeeds with the determined second slope.

2. The controller as defined by claim 1, wherein the controller is further configured to control the measurement system such that the pressure applicator increases the applied pressure over time also in a zeroth measurement time period (T.sub.0) with a zeroth slope, wherein T.sub.0 is temporally arranged before T.sub.1, wherein the first slope is smaller than or equal to the zeroth slope, and the pressure sensor measures TP on the skin also during the zeroth measurement time period, wherein TP comprises at least one pressure pulse, wherein the controller is further configured to determine a heart rate value (HR) being indicative of the heart rate of the subject based on the at least one pressure pulse of TP measured in T.sub.0 and to, after the determination of HR, determine the first slope based on HR, and control the measurement system such that T.sub. 1 succeeds with the determined first slope.

3. The controller as defined by claim 2, wherein the controller is configured to determine HR also during T.sub.1 and to modify the first slope based on HR determined during the first measurement time period.

4. The controller as defined by claim 1, wherein the controller is configured such that the forming of TPW_F-curve based on the several start values (TPWP_F) includes a low pass filtering of the several start values (TPWP_F).

5. The controller as defined by claim 4, wherein the controller is configured such that the low pass filtering of the several start values (TPWP_F) and the low pass filtering of the several blood pressure determination values (TPWP_S) both use a filtering window, wherein the filtering window for low pass filtering the several start values (TPWP_F) has a window length being smaller than a window length of the filtering window for low pass filtering the several blood pressure determination values (TPWP_S).

6. The controller as defined by claim 1, wherein the controller is configured to, in order to determine for a respective pressure pulse at least one feature, provide a feature determination pulse based on the respective pressure pulse, and determine at least one of the following features:

TPP t(pulse)

TPA,

TPA.norm

W50

TPA.top, and

TPA.top.norm)

under an upper part of the respective feature determination pulse.

7. The controller defined by claim 1, wherein the controller is configured to stop the second measurement time period as soon as a provided respiration rate value (RR) indicates that the second measurement time period covers 3.5 respiration or ventilation cycles (VC) and/or a predetermined maximum measurement time period has been reached and/or a maximum mean pressure value has been reached.

8. The controller as defined by claim 7, wherein the controller is configured to modify the second slope based on RR determined during the second measurement time period and/or depending on the maximum mean pressure value.

9. The controller as defined by claim 1, wherein the controller is configured to determine:

for a respective pressure pulse measured in the second measurement time period a blood pressure determination value (TPWP_S) based on at least one of the at least one determined feature (TPP, t(Pulse), TPA, TPA.norm, W50, TPA.top, TPA.top.norm) such that for several pressure pulses, which are present at different times, several blood pressure determination values (TPWP_S) are determined, wherein the several blood pressure determination values (TPWP_S) determined for the several pressure pulses and hence for several times form a blood pressure determination curve (TPW_S-curve), the blood pressure value based on the blood pressure determination curve (TPW_S-curve).

10. The controller as defined by claim 9, wherein the controller is configured such that the forming of the blood pressure determination curve (TPW_S-curve) based on the several blood pressure determination values (TPWP_S) includes a low pass filtering of the several blood pressure determination values (TPWP_S).

11. The controller as defined by claim 1, wherein the controller is configured to further determine a hemodynamic monitoring parameter based on the pressure measured in the second measurement time period.

12. A measurement system for measuring blood pressure of a subject, wherein the measurement system comprises:

a controller as defined in claim 1, a shell configured to encase a part of the subject, through which blood flows, a pressure applicator configured to apply, from outside the shell, pressure to the shell and thereby to the encased part of the subject, a pressure sensor configured to measure the pressure (TP) on the skin of the encased part of the subject.

13. A control method for controlling a measurement system as defined by claim 12, wherein the control method includes:

increasing the applied pressure over time in a first measurement time period (T.sub.1) with a first slope and in a second measurement time period (T.sub.2) with a second slope by using the pressure applicator, wherein the first measurement time period (T.sub.1) and the second measurement time period (T.sub.2) are temporally arranged in this sequence, measuring the pressure (TP) on the skin during the first and second measurement time periods by using the pressure sensor, wherein the measured pressure (TP) comprises a plurality of pressure pulses, determining, in the first measurement time period (T.sub.1), for each pressure pulse of at least some of the plurality of pressure pulses, at least one feature (TPP, t(Pulse), TPA, TPA.norm, W50, TPA.top, TPA.top.norm), which characterizes the respective pressure pulse, wherein TPP denotes the difference between a respective pressure pulse's maximum systolic pressure (TPsys) and the respective pressure pulse's pressure at the end-diastolic point (TPdia), t(Pulse) denotes the duration of the respective pressure pulse, TPA denotes the entire area of the respective pressure pulse, TPA.norm denotes a normalized area of the respective pressure pulse, W50 denotes the width at half maximum of the respective pressure pulse, TPA.top denotes an upper area under an upper part of the respective pressure pulse, and TPA.top.norm denotes a normalized upper area under an upper part of the respective pressure pulse;

determining for each of the at least some of the plurality of pressure pulses, a start value (TPWP_F), to be used for determining the start of the second measurement time period, based on the at least one feature (TPP, t(Pulse), TPA,TPA.norm, W50, TPA.top, TPA.top.norm), which has been determined for the respective pressure pulse, such that for several pressure pulses, which are present at different times, several start values (TPWP_F) are determined, forming a start curve (TPW_F-curve), to be used for determining the start of the second measurement time period, based on the several start values (TPWP_F), and controlling, after the start curve (TPW_F-curve) has reached a first maximum, the measurement system such that the second measurement time period succeeds, determining a blood pressure value (niBP) based on the pressure (TP) measured in the second measurement time period (T.sub.2), and determining, in the first measurement time period (T.sub.1), a first blood pressure value based on the start curve (TPW_F-curve), determining the second slope based on the determined first blood pressure value and controlling, after the start curve (TPW_F-curve) has reached a first maximum, the measurement system such that the second measurement time period (T.sub.2) succeeds with the determined second slope.

14. A computer program for controlling a measurement system as defined by claim 12, the computer program comprising program code means for causing the measurement system, when run on the controller of the measurement system, to increase the applied pressure over time in a first measurement time period (T.sub.1) with a first slope and in a second measurement time period (T.sub.2), with a second slope by using the pressure applicator, wherein the first measurement time period (T.sub.1) and the second measurement time period (T.sub.2) are temporally arranged in this sequence, measure the pressure (TP) on the skin during the first and second measurement time periods by using the pressure sensor, wherein the measured pressure (TP) comprises a plurality of pressure pulses, determine, in the first measurement time period (T.sub.1), for each pressure pulse of at least some of the plurality of pressure pulses, at least one feature (TPP, t(Pulse), TPA, TPA.norm, W50, TPA.top, TPA.top.norm), which characterizes the respective pressure pulse, wherein TPP denotes the difference between a respective pressure pulse's maximum systolic pressure (TPsys) and the respective pressure pulse's pressure at the end-diastolic point (TPdia), t(Pulse) denotes the duration of the respective pressure pulse, TPA denotes the entire area of the respective pressure pulse, TPA.norm denotes a normalized area of the respective pressure pulse.

W50 denotes the width at half maximum of the respective pressure pulse,

TPA.top denotes an upper area under an upper part of the respective pressure pulse, and TPA.top.norm denotes a normalized upper area under an upper part of the respective pressure pulse;

determining for each of the at least some of the plurality of pressure pulses, a start value (TPWP_F), to be used for determining the start of the second measurement time period, based on the at least one feature (TPP, t(Pulse), TPA, TPA.norm, W50, TPA.top, TPA.top.norm), which has been determined for the respective pressure pulse, such that for several pressure pulses, which are present at different times, several start values (TPWP_F) are determined, forming a start curve (TPW_F-curve), to be used for determining the start of the second measurement time period based on the several start values (TPWP_F), and controlling after the start curve (TPW_F-curve) has reached a first maximum, the measurement system such that the second measurement time period succeeds, determine a blood pressure value (mBP) based on the pressure (TP) measured in the second measurement time period (T.sub.2), and determine, in the first measurement time period (T.sub.1), a first blood pressure value based on the start curve (TPW_F-curve), determining the second slope based on the determined first blood pressure value and controlling, after the start curve (TPW_F-curve) has reached a first maximum, the measurement system such that the second measurement time period (T.sub.2) succeeds with the determined second slope.

* * * * *